US006537299B1

(12) United States Patent
Hogendijk et al.

(10) Patent No.: US 6,537,299 B1
(45) Date of Patent: *Mar. 25, 2003

(54) INTRAVASCULAR HEMOSTASIS DEVICE AND METHOD

(75) Inventors: Michael Hogendijk, Palo Alto, CA (US); Paul M. Paspa, Sunnyvale, CA (US); Hugh L. Narciso, Jr., Mountain View, CA (US)

(73) Assignee: Ethicon, Inc., Somerville, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/286,495

(22) Filed: Apr. 5, 1999

(51) Int. Cl.[7] .............................................. A61B 17/04
(52) U.S. Cl. ...................................................... 606/213
(58) Field of Search .............................. 606/213, 151, 606/153, 154, 155

(56) References Cited

U.S. PATENT DOCUMENTS 5,690,674 A * 11/1997 Diaz .......................... 606/213
5,944,730 A * 8/1999 Nobles et al. ............... 606/151

FOREIGN PATENT DOCUMENTS

| EP | 0 544 485 A1 | 2/1993 |
|----|----|----|
| EP | 0895753 | 2/1999 |
| WO | WO 97/40881 | 11/1997 |
| WO | WO 97/47261 | 12/1997 |
| WO | WO 98/52475 | 12/1998 |

OTHER PUBLICATIONS

Robicsek, Francis M.D., "Aortic Spoon–Jaw Clamp For Aorto–Saphenous Vein Anastomosis," J. Card. Surg. 1995; 10:583–585.

* cited by examiner

Primary Examiner—Gary Jackson

(57) ABSTRACT

Several embodiments of an intravascular hemostasis device are disclosed which in one embodiment generally comprises at least a first elongated tubular member having a proximal end portion and a distal end portion, and a flexible, deformable sealing member coupled to the distal end portion of the elongated tubular member which has at least a first preformed expanded state, the sealing member being at least partially radially compressible to at least a first compressed state for insertion of the sealing member into an opening in a blood vessel, the sealing member being radially expandable from its compressed state to its expanded state after the sealing member is inserted into the opening in the vessel in which the sealing member is adapted to seal against an inner wall of the blood vessel around the opening.

55 Claims, 23 Drawing Sheets

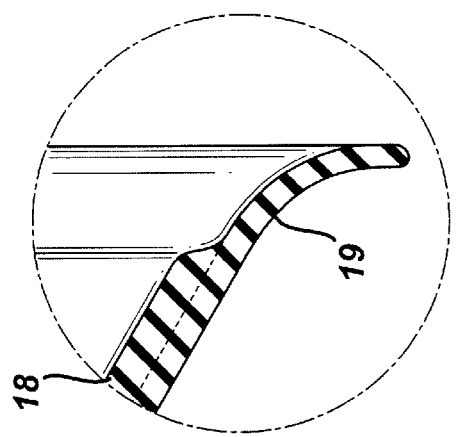
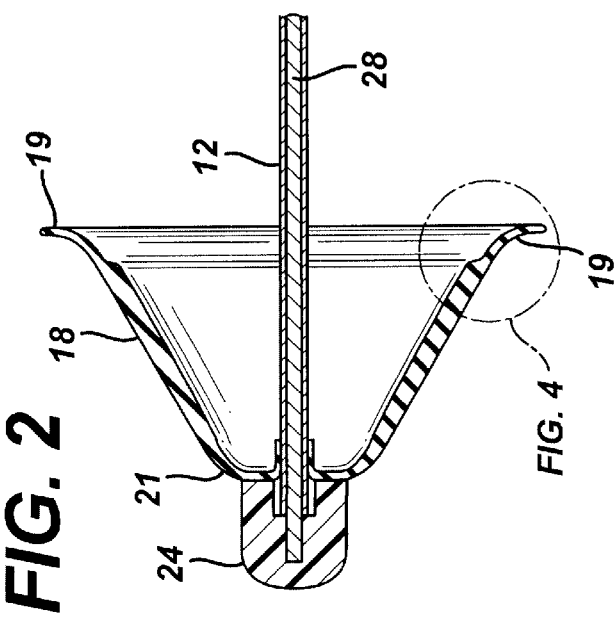
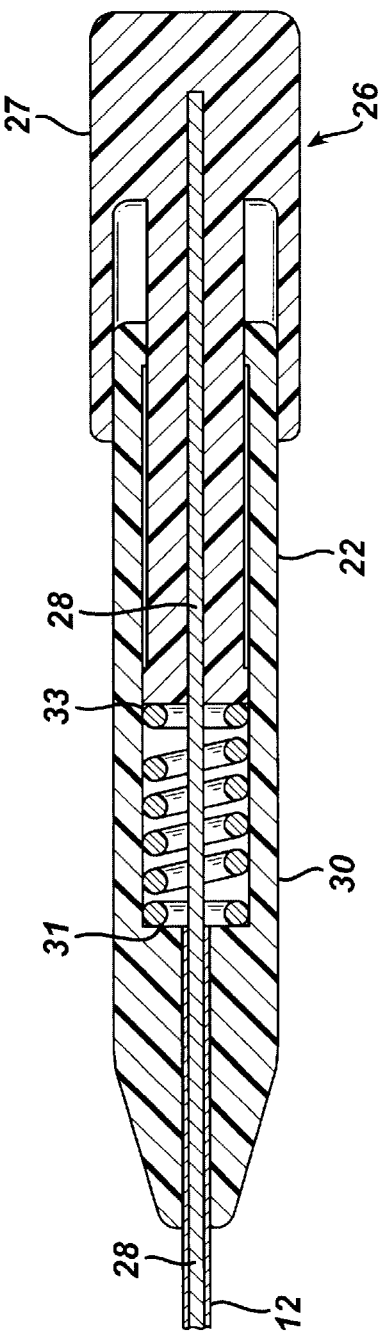

FIG. 5A
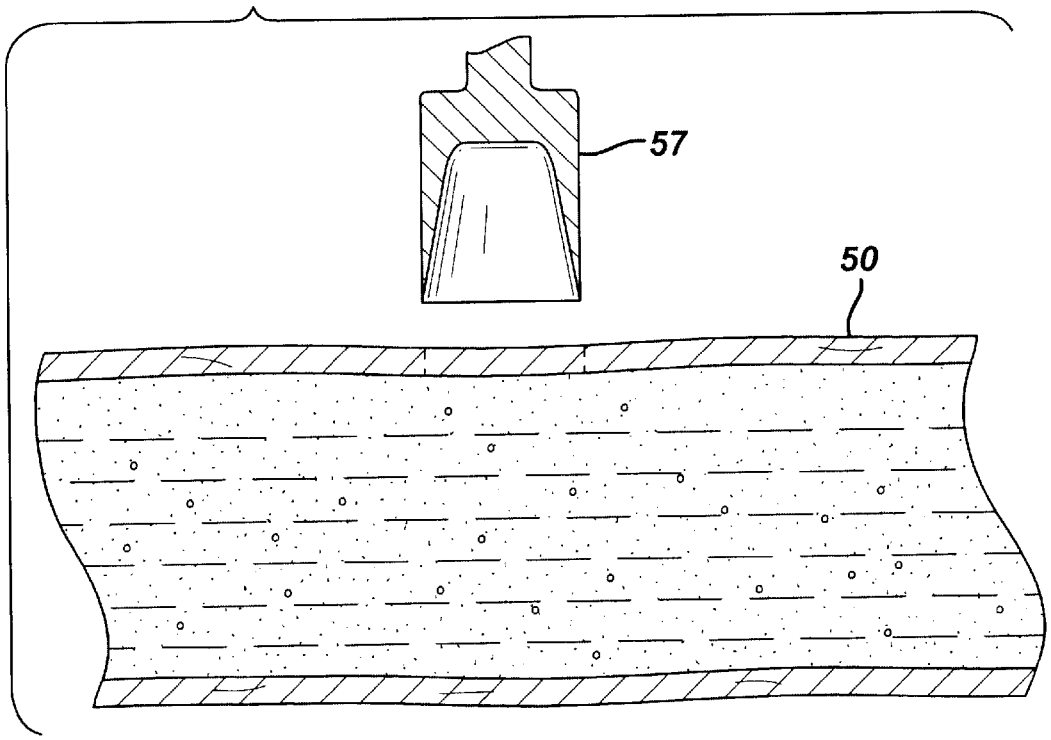
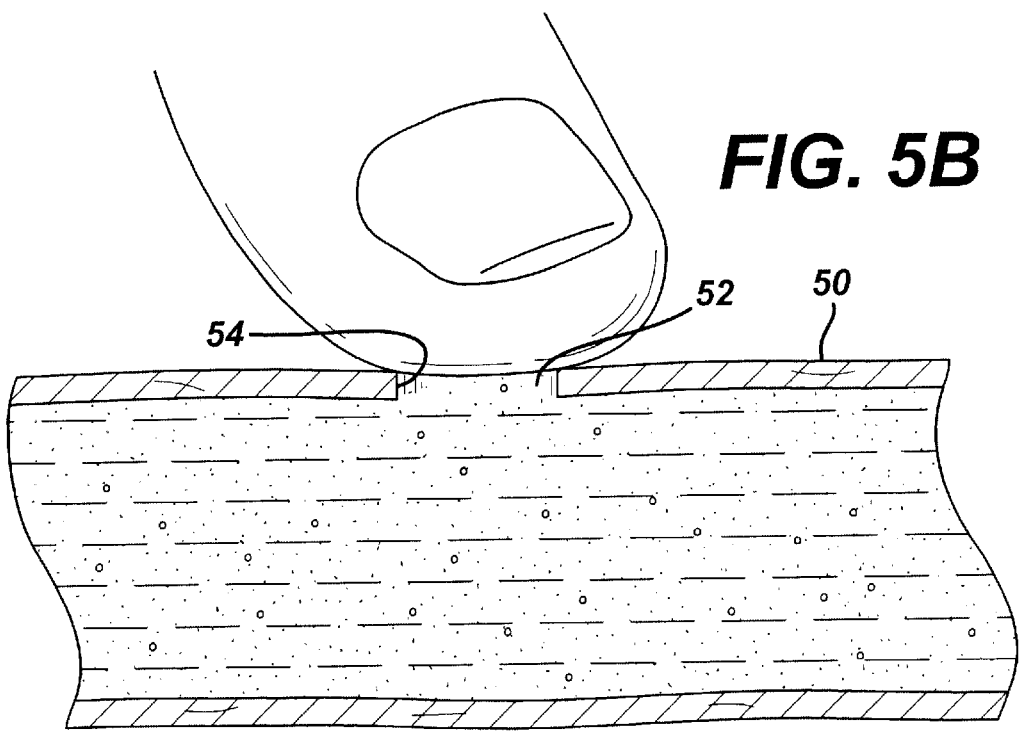
FIG. 5B

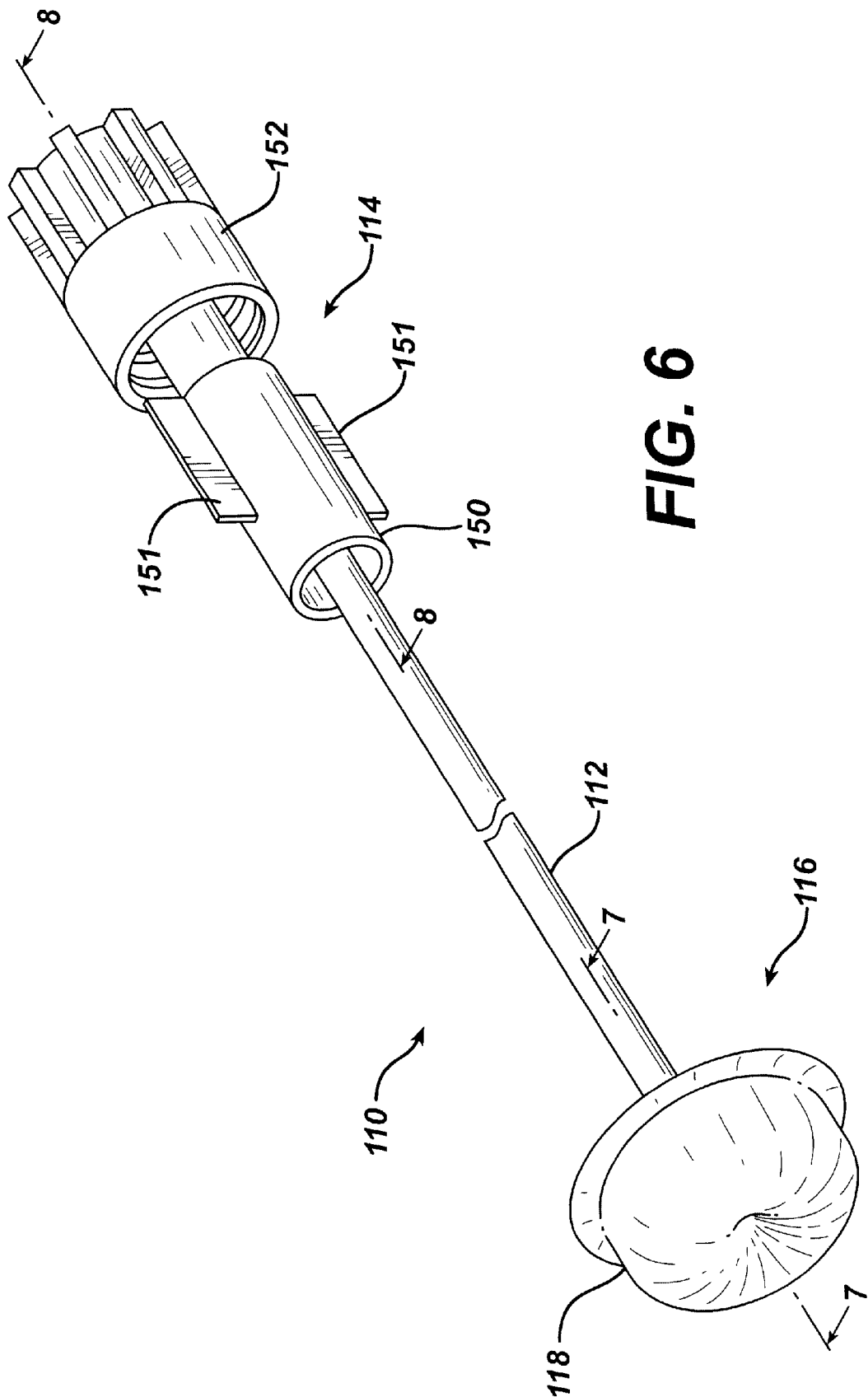

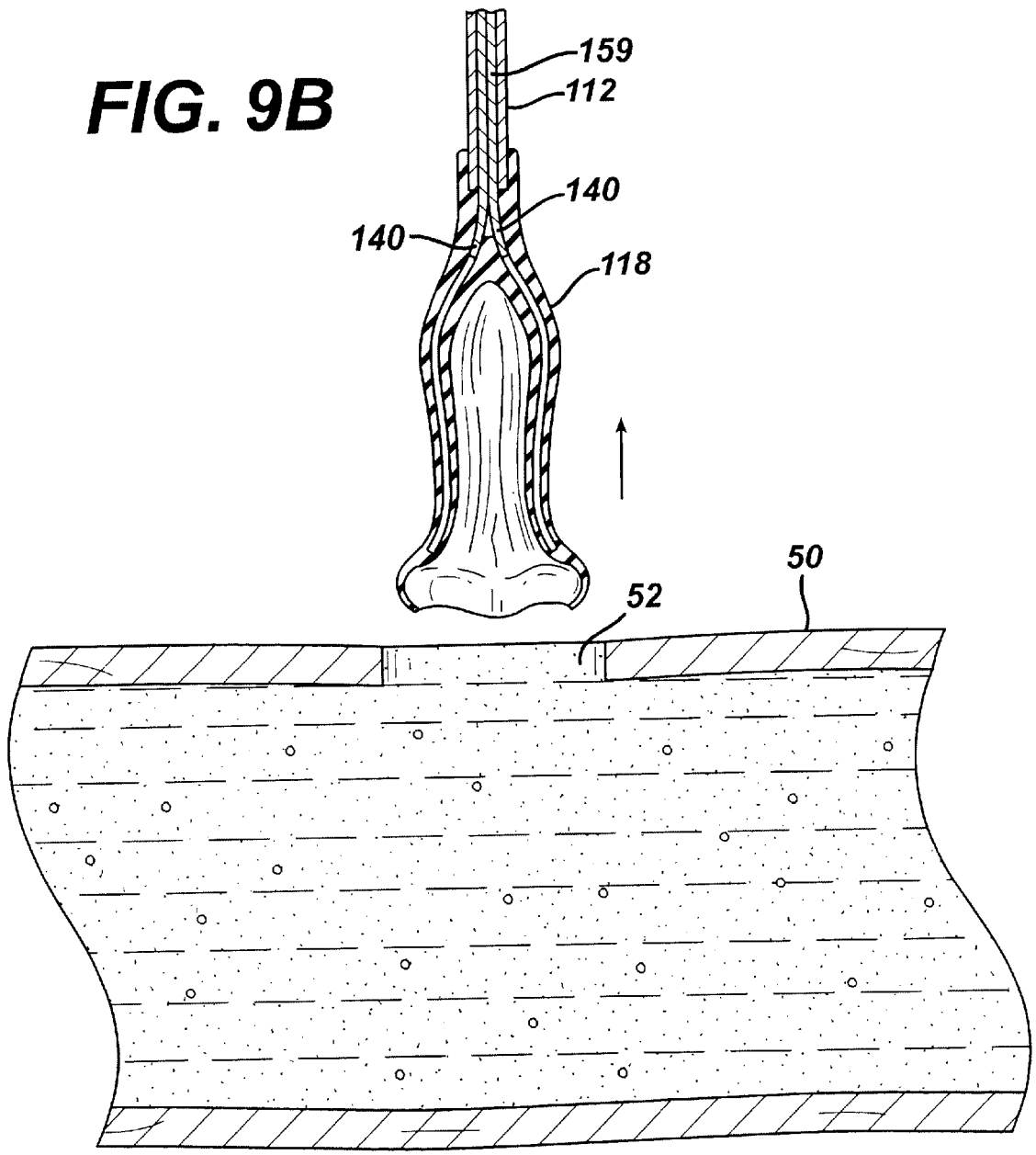

FIG. 10C
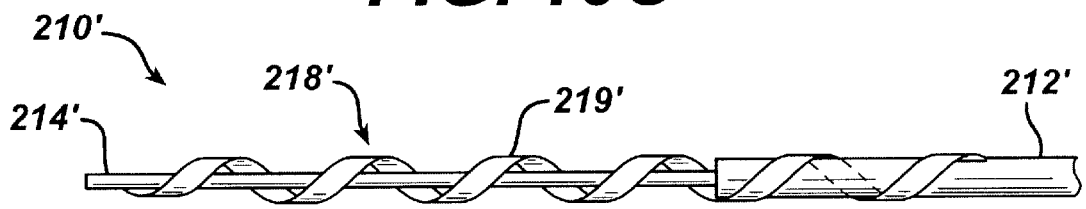
FIG. 10D
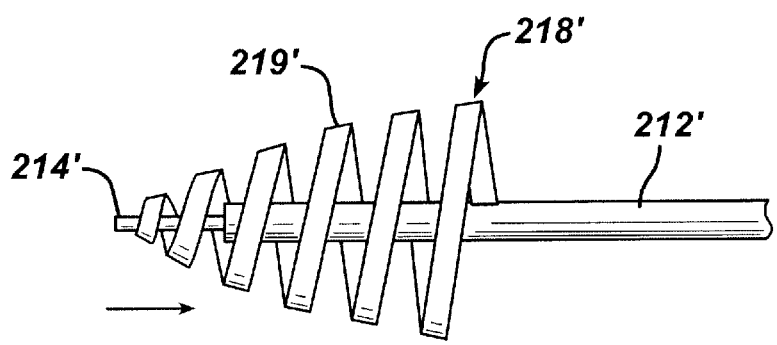
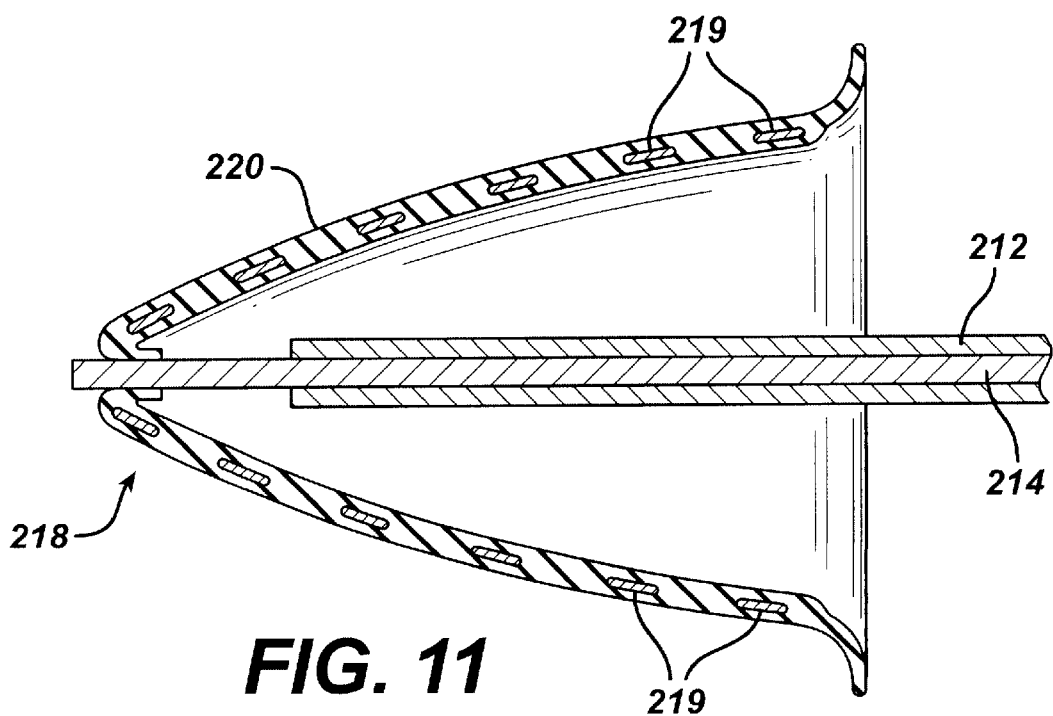
FIG. 11

INTRAVASCULAR HEMOSTASIS DEVICE AND METHOD

FIELD OF THE INVENTION

The present invention relates generally to medical and surgical devices and methods thereof. Specifically, the present invention relates to an intravascular hemostasis device and method used to create a blood-free area in a portion of a blood vessel, such as the aorta, or a body organ, during a medical or surgical procedure, such as a proximal anastomosis procedure, while still permitting the flow of blood within the vessel.

BACKGROUND OF THE INVENTION

A manifestation of coronary artery disease is the build-up of plaque on the inner walls of the coronary arteries, which causes narrowing or complete closure of these arteries, resulting in insufficient blood flow. This deprives the heart muscle of oxygen and nutrients, leading to ischemia, possible myocardial infarction and even death. Surgery to alleviate this problem often involves creating an anastomosis between a coronary artery and a graft vessel to restore a blood flow path to essential tissues. An anastomosis is a surgical procedure by which two vascular structures, such as a graft vessel and a coronary artery, are interconnected.

Conventional coronary bypass graft procedures require that a source of arterial blood be prepared for subsequent bypass connection to the diseased artery. An arterial graft can be used to provide a source of blood flow, or a free vessel graft may be used and connected at the proximal end to a source of blood flow. Preferably, the source of blood flow is any one of a number of existing arteries that are dissected in preparation for the bypass graft procedure. In many instances, it is preferred to use either the left or right internal mammary artery. In multiple bypass procedures, it may be necessary to use free vein graft vessels such as the saphenous vein of the leg or the cephalic or basilic veins in the arm. Alternatively, free arterial grafts can be used when the leg or arm veins are unavailable or are unsuitable, such as the gastroepiploic artery in the abdomen, and other arteries harvested from the patient's body. Synthetic graft materials, such as Dacron or Gortex grafts, can be used as well. If a free graft vessel is used, the upstream end (proximal) of the dissected vessel, which is the arterial blood source, will be secured to the aorta to provide the desired bypass blood flow in a proximal anastomosis procedure, and the downstream end (distal) of the dissected vessel will be connected to the target vessel in a distal anastomosis procedure.

Currently, the conventional practice in performing coronary artery bypass graft surgical procedures is to open the chest by making a longitudinal incision along the sternum (e.g., a partial or median sternotomy), placing the patient on a cardiopulmonary bypass (CPB) (heart-lung) machine, stopping the heart from beating by administering a conventional cardioplegia solution (e.g., a potassium chloride solution) to the heart, and then attaching the coronary artery bypass graft(s) to the coronary arteries (and/or aorta in the case of the proximal end of a free graft vessel). The heart-lung machine is needed to maintain the blood circulation through the patient and to provide gas and heat exchange surfaces. However, there are numerous complications associated with conventional open-chest procedures, many of which are related to the use of a heart-lung machine. The use of a heart-lung machine has been shown to be the cause of many of the complications that have been reported in conventional coronary artery bypass graft procedures, such as complement and neutrophil activation, adverse neuropsychologic effects, coagulopathy, and even stroke. The period of CPB should be minimized, if not avoided altogether, to reduce patient morbidity.

A current trend in coronary artery bypass graft surgery is to utilize a minimally invasive surgical technique. Minimally invasive techniques (i.e., surgical techniques that avoid the partial or median sternotomy and/or the use of CPB) have been developed to attempt to reduce or eliminate some of the more serious complications of conventional open-chest cardiac surgery techniques, such as the morbidity associated with the use of CPB. One approach to minimally invasive cardiac surgery is an endoscopic procedure in which access to the heart is gained through several small openings, or ports, in the chest wall of a patient. The endoscopic method allows surgeons to stop the heart without cracking the chest by utilizing a series of internal catheters to stop blood flow through the aorta and to administer a conventional cardioplegia solution (e.g., a potassium chloride solution) to facilitate stopping the heart. The cardioplegia solution paralyzes the electrical activity of the heart and renders the heart substantially totally motionless during the surgery. The endoscopic approach utilizes groin cannulation to establish CPB which takes over the function of the heart and lungs by circulating oxygenated blood throughout the body. After CPB is started, an intraaortic balloon catheter that functions as an internal aortic clamp by means of an expandable balloon at its distal end is used to occlude blood flow in the ascending aorta from within. A full description of an example of one preferred endoscopic technique is found in U. S. Pat. No. 5,452,733, the complete disclosure of which is incorporated by reference herein. A primary drawback of endoscopic cardiac surgery procedures, however, is that such procedures do not avoid the damaging effects of CPB generally described above.

An approach to minimally invasive cardiac surgery that avoids CPB and aortic cross-clamping is minimally invasive direct coronary artery bypass grafting (MIDCAB) on a beating heart. Using this method, the heart typically is accessed through a minithoracotomy (i.e., a 6 to 8 cm incision in the patient's chest) which also avoids the sternal splitting incision of conventional cardiac surgery. The heart may also be accessed through a partial or median sternotomy in an off-pump coronary artery bypass graft (OPCAB) technique which gives the surgeon greater direct acces to the heart. In both the MIDCAB and OPCAB procedures, the anastomosis procedure is then performed under direct vision on the beating heart without the use of CPB or potassium chloride cardioplegia. However, there are many obstacles to precise coronary anastomosis during MIDCAB or OPCAB on a beating heart. In particular, the constant translational motion of the heart and bleeding from the opening in the coronary artery hinder precise suture placement in the often tiny coronary vessel.

In response to problems associated with the above-described minimally invasive surgical techniques, a new minimally invasive surgical platform known as the Transarrest™ platform has been developed to minimize the cardiac motion of the beating heart while avoiding the need for CPB, aortic cross-clamping and conventional cardioplegia. The Transarrest™ platform employs a novel pharmaceutical approach to stabilizing the heart. This revolutionary pharmaceutical approach to cardiac stabilization is fully described in co-pending patent application for "Compositions, Apparatus and Methods For Facilitating Surgical Procedures," Ser. No. 09/131,075, filed Aug. 7, 1998 and invented by Francis G. Duhaylongsod, M.D, the entire contents of which are expressly incorporated by reference herein. As described therein, pharmaceutical compositions, devices, and methods are provided which are useful for medical and surgical procedures which require precise control of cardiac contraction, such as minimally invasive coronary bypass procedures. Generally, the Transarrest™ platform involves the administration of a novel cardioplegia solution which provides for precise heart rate and rhythm control management while maintaining the ability of the heart to be electrically paced (i.e., which does not paralyze the electrical activity of the heart as with conventional cardioplegia solutions). Specifically, the novel cardioplegia solution comprises a pharmaceutical composition which is capable of inducing reversible ventricular asystole in the heart of a patient, while maintaining the ability of the heart to be electrically paced. "Reversible ventricular asystole" refers to a state wherein autonomous electrical conduction and escape rhythms in the ventricle are suppressed. A state of the heart may be induced wherein the heart is temporarily slowed to at least about 25 beats per minute or less, and often about 12 beats per minute or less. The induced ventricular asystole is reversible and after reversal, the heart functions are restored, and the heart is capable of continuing autonomous function.

The pharmaceutical composition may preferably include, for example, an atrioventricular ("AV") node blocker and a beta blocker. As used herein, the term "AV node blocker" refers to a compound capable of reversibly suppressing autonomous electrical conduction at the AV node, while still allowing the heart to be electrically paced to maintain cardiac output. Preferably, the AV node blocker, or the composition comprising the AV node blocker, reduces or blocks ventricular escape beats and cardiac impulse transmission at the AV node of the heart, while the effect on depolarization of the pacemaker cells of the heart is minimal or nonexistent. The beta blocker is provided in one embodiment in an amount sufficient to substantially reduce the amount of AV node blocker required to induce ventricular asystole. For example, the AV node blocker may be present in the composition in an amount which is 50% or less by weight, or optionally about 1 to 20% by weight of the amount of AV node blocker alone required to induce ventricular asystole.

The pharmaceutical composition, such as an AV node blocker, capable of causing ventricular asystole in a preferred embodiment is a cholingeric agent such as carbachol, although other cholingeric agents may be used as well such as acetylcholine, methacholine, bethanechol, arecoline, norarecoline, neostigmine, pyridostigmine, and other agents that increase cyclic GMP levels by direct or indirect cholinergic receptor stimulation. Other exemplary AV node blockers include calcium channel blockers, adenosine A1 receptor agonists, adenosine deaminase inhibitors, cholinesterase inhibitors, monamine oxidase inhibitors, serotoninergic agonists, antiarrythmics, cardiac glycosides, and local anesthetics. Examples of these AV node blockers include verapamil, diltiazem, lidocaine, procaine, procainamide, quinidine, choloroquine, amiodarone, pilocarpine, ethmozine, propafenone, flecainide, encainide, tranylcypromine, serotonin, adenosine, digoxin, digitalis, dipyridamole, ibutilide, zapranest, sotalol, metoclopromide and combinations thereof.

In the preferred embodiment, the beta blocker is propranolol, although other suitable beta blockers may be used as well. Other exemplary beta blockers include atenolol, acebutolol, labetalol, metoprolol, nadolol, oxprenolol, penbutolol, pindolol, sotalol and timolol, and any combinations or pharmaceutically acceptable salts thereof. Alternatively, celiprolol, betaxolol, bevantolol, bisoprolol, esmololol, alprenolol, carterolol, nadolol, or teratolol may be used. The beta blocker may be any naturally occurring or synthetic analogue capable of blocking beta-adrenergic receptor sites. The administration of the beta blocker is preferably prior to, or contemporaneously with, the administration of the cholinergic agent, and results in a synergistic effect between the beta blocker and the cholinergic agent. The use of a cholinergic agent, such as carbachol, in combination with a beta-blocker, such as propranolol, produces ventricular asystole at significantly reduced dosages compared to the cholinergic agent used alone, while maintaining a short half-life and rapid onset of effect.

In one embodiment to induce reversible ventricular asystole in a patient, the beta-blocker propranolol and the AV node blocker carbachol are serially administered in an initial intracoronary bolus to the right or left coronary artery to induce reversible ventricular asystole of the heart, and then carbachol is administered as a periodic (e.g. one or more bolus infusions) or continuous intracoronary infusion to maintain ventricular asystole during the course of the surgical procedure. For example, an intracoronary injection of about 0.5 to 4 mg, for example about 1 mg, of propranolol is administered by intracoronary infusion over a time period of about 0.5 to 3.0 minutes, e.g., about 1 minute, preferably followed by a saline flush, such as 2 mL saline flush. This is followed by an intracoronary bolus injection of about 0.01 to 0.5 mg, e.g., about 0.025 to 0.3 mg, e.g., about 0.1 mg carbachol administered over about 0.5 to 3.0 minutes, e.g., about 1 minute, to initially induce ventricular asystole. To maintain ventricular asystole, carbachol is administered as one or more bolus administrations (e.g., about 0.05 mg/bolus) or as an intracoronary infusion to the right or left coronary artery at a rate of about 0.01 to 0.3 mg/min, e.g., about 0.025 to 0.3 mg/min, for example, about 0.01 to 0.1 mg/min, e.g., about 0.05 to 0.1 mg/min, e.g., about 0.0825 mg/min, for a time period of about 5 to 90 minutes, preferably about 30 to 90 minutes, depending on the length of the procedure. A dosage amount of about 1.0 mg of phenylephrine may be administered to control the hypotensive effects associated with carbachol administration. Atropine (about 1 mg) may be used to reverse ventricular asystole and restore the heart to its normal function.

Electrical pacing wires are connected to the right ventricle and/or left ventricle and/or atria and are used to pace the heart using a novel foot-actuated pacer control system to maintain the patient's blood circulation during the periods in which the surgeon is temporarily not performing the surgical procedure. Thus, for example, in a coronary bypass procedure, the surgeon can control the pacing of the heart with a convenient foot pedal and can controllably stop the heart as sutures are placed in the vessel walls. The pharmaceutical compositions, devices and methods for drug delivery, and systems for pacing the heart, give a surgeon complete control of the beating heart. The Transarrest™ procedure described above can be used to facilitate any surgical procedure which requires intermittent stoppage of the heart or elimination of movements caused by pulsatile blood flow, whether access is gained to the body cavity via a partial or median sternotomy incision, via a mini-thoracotomy incision, or via one or more small incisions or ports in the chest wall.

In performing a coronary bypass graft procedure to the aorta using the Transarrest™ procedure described above (or any of the other open-chest or minimally invasive approaches to cardiac surgery described above), it is necessary to create a hole in the aorta where a proximal anastomosis graft is to be made. To prevent blood loss through this hole, typically the aorta is clamped with a conventional U-shaped "side-biting" clamp to temporarily stop or substantially minimize the blood flow through the aorta. Another surgical technique involves the use of the aortic cross-clamp which is employed when conventional cardioplegia is administered. A problem with these techniques is that the compressive forces of the clamp increase the risk that plaque or other atherosclerotic material accumulated on the walls of the aorta will be released into the blood stream, which can lead to embolic events such as myocardial infarction or cerebral deficits such as stroke.

Thus, it would be desirable to provide an anastomosis assist device, preferably of relatively simple construction and cost, which is designed to eliminate clamping during a proximal anastomosis procedure in which a free graft vessel is grafted to the aorta. Examples of previous attempts to reduce the risks of a proximal anastomosis procedure by avoiding the untoward effects of aortic clamping are provided in PCT Patent Application WO 97/40881 to Jonkman et al., PCT Patent Application No. WO 98/52475 to Nobles et al., and European Patent Application No. EP 0895753 to Borst et al., the entire contents of which are expressly incorporated by reference herein. The present invention involves improvements to devices and methods for sealing an opening in a blood vessel, such as in the aorta where an anastomosis graft is to be made, while still permitting the flow of blood through the blood vessel.

SUMMARY OF THE INVENTION

The present invention involves several embodiments of an intravascular hemostasis device and method which are adapted to seal an opening in a blood vessel, such as an aorta, while still permitting blood flow through the vessel. The present invention is particularly well-suited to facilitate a proximal anastomosis procedure in which a free end of a graft vessel, such as a saphenous vein, is secured to an opening in a side wall of the aorta. However, those of ordinary skill in the art will recognize that the present invention can be used in any medical or surgical procedure in which it is necessary to form a seal against a wall of a blood vessel or other body organ.

According to a first aspect of the present invention, an intravascular hemo stasis device is disclosed which generally comprises at least a first elongated tubular member having a proximal end portion and a distal end portion, and a flexible, deformnable sealing member coupled to the distal end portion of the elongated tubular member which has at least a first pre-formed expanded state, the sealing member being at least partially radially compressible to at least a first compressed state for insertion of the sealing member into an opening in a blood vessel, the sealing member being radially selfexpandable from its compressed state to its expanded state after the sealing member is inserted into the opening in the vessel in which the sealing member is adapted to substantially seal against an inner wall of the blood vessel around the opening. Advantageously, the sealing member has a pre-formed cup-shaped configuration in its first expanded state in which the sealing member has a circumferential rim portion which is adapted to form a seal against the inner wall of the blood vessel around the opening.

In a preferred embodiment, the sealing member is moveable to an inverted configuration to facilitate its removal from the blood vessel in which the sealing member has a second expanded state which is a mirror image of its first expanded state when a sufficient force is applied to the sealing member. For example, the sealing member is configured such that when a sufficient force is applied to the sealing member by the inner wall of the blood vessel as the elongated tubular member is moved away (e.g., proximally) from the blood vessel, the sealing member will invert to its inverted configuration. The sealing member is at least partially radially compressible from its second expanded state to a second compressed state to allow for removal of the sealing member from the blood vessel through the opening in the blood vessel.

Advantageously, the intravascular hemostasis device in a preferred embodiment also includes a support element coupled to or immediately adjacent the sealing member to provide enhanced rigidity to the sealing member when in its expanded state to prevent the sealing member from inadvertently inverting to its inverted configuration during use of the device and to provide enhanced rigidity to the sealing member to enhance its sealing function. For example, in one embodiment, the intravascular hemostasis device includes a support hub located adjacent to the sealing member and a second elongated tubular member slidably coupled to the first elongated tubular member, with the support hub being coupled to a distal end portion of the second elongated tubular member. The support hub is spring-biased in its natural configuration to engage a distal shoulder portion of the sealing member to provide enhanced support and rigidity thereto. An actuator is operatively coupled to the second elongated tubular member. The support hub is moveable axially relative to the sealing member upon actuation of the actuator which facilitates inversion and removal of the sealing member from the blood vessel through the opening in the wall of the blood vessel.

In an alternative embodiment, the support element comprises a plurality of wires movably embedded within the sealing member which provide support to the sealing member in its expanded state. An actuator is operatively coupled to the plurality of wires and is operable to withdraw the plurality of wires externally from the sealing member to facilitate inversion and removal of the sealing member from the blood vessel through the opening in the wall of the blood vessel. The sealing member may also include retaining means for retaining the sealing member in abutting engagement with an interior wall of the blood vessel to allow for substantially hands-free operation of the device. The retaining means, can include, among other things, a suction force which is applied to the sealing member to retain the sealing member in abutting engagement with the interior wall of the vessel around the opening therein. Other types of retaining means are further disclosed below.

According to a further aspect of the present invention, an intravascular hemostasis device is disclosed which generally comprises a first elongated tubular member, a second elongated tubular member rotatably coupled to the first elongated tubular member, a flexible sealing member coupled to distal end portions of the first and second elongated tubular members, the sealing member being moveable between a narrow, collapsed configuration in which the sealing member is adapted to be inserted into and removed from a blood vessel through an opening in a wall of the blood vessel, and an expanded configuration in which the sealing member is adapted to form a seal against an inner wall of the blood vessel around the opening, and wherein the sealing member is selectively adjustable between its narrow, collapsed configuration and its expanded configuration upon relative rotational movement of the first and second elongated tubular members from outside the blood vessel. The sealing member can comprise a wire or ribbon which is spiralled about the distal end portions of the first and second elongated tubular members. The wire or ribbon is at least partially coated with a polyurethane material to make it impermeable to fluid flow. An actuator is coupled to a proximal end portion of the second elongated tubular member and is operable to rotate the second elongated tubular member relative to the first elongated tubular member to selectively move the spiralled wire or ribbon between its narrow, collapsed configuration and its expanded configuration in which the wire or ribbon assumes a general cup-shaped configuration which is adapted to seal against the opening in the wall of the vessel.

In yet another alternative embodiment of the invention, an intravascular hemostasis device is disclosed which generally comprises a first elongated tubular member, a second elongated tubular member movably coupled to the first elongated tubular member, a flexible sealing member coupled to a distal end portion of the second elongated tubular member, the sealing member being moveable between a narrow, collapsed configuration in which the sealing member is adapted to be inserted into and removed from a blood vessel through an opening in a wall of the blood vessel, and an expanded configuration in which the sealing member is adapted to form a seal against an inner wall of the blood vessel around the opening, and wherein the sealing member is selectively adjustable between its narrow, collapsed configuration and its expanded configuration upon relative axial movement of the first and second elongated tubular members from outside the blood vessel. The sealing member may comprise a plurality of spaced-apart wire loops that are coated with a polyurethane material to form an impermeable barrier to fluid flow. The plurality of wire loops are preformed to assume an expanded configuration when extending from the first elongated tubular member, and can be withdrawn into the first elongated tubular member to assume a collapsed configuration upon actuation of the second elongated tubular member.

According to another aspect of the present invention, several methods of performing a coronary bypass procedure are disclosed which in one embodiment generally comprises providing a graft vessel having a first free end and a second free end; providing an intravascular hemostasis device comprising an elongated tubular member having a proximal end portion, a distal end portion, and a flexible, deformable sealing member coupled to the elongated tubular body adjacent the distal end portion, the sealing member being adapted for relative movement between a natural pre-formed first expanded state and a compressed state; forming an opening in a side wall of an aorta; inserting the distal end of the elongated tubular body and the sealing member into the aorta through the opening while the sealing member is in its expanded state such that the side wall of the aorta around the opening exerts an inwardly directed force over at least a portion of the sealing member to cause it to move from its expanded state to its compressed state; moving the elongated tubular body proximally away from the aorta following radial expansion of the sealing member into its expanded state within the aorta until the sealing member in its expanded state contacts the interior of the side wall of the aorta and substantially seals the opening from blood flowing through the aorta; at least partially attaching the first free end of the graft vessel to the side wall of the aorta about the opening; and removing the intravascular hemostasis device from the aorta. Other methods for sealing an opening in a blood vessel or body organ are described in detail below and in the appended claims.

The invention described below solves the deficiencies of the prior art and offers a number of other features and advantages that will be apparent to one of ordinary skill in the art from the following detailed description, accompanying figures and appended claims.

BRIEF DESCRIPTION OF THE DRAWINGS

FIG. 2 is a cross-sectional view of the distal end portion of the intravascular hemostasis device of FIG. 1 showing the configuration of the flexible sealing member.

FIG. 3 is a cross-sectional view of the proximal end portion of the intravascular hemostasis device of FIG. 1.

FIG. 4 is an exploded cross-sectional view of the circumferential rim portion of the sealing member of the intravascular hemostasis device of FIG. 1.

FIG. 5A is a cross-sectional view showing an opening being made in the side wall of an aorta with a conventional circular aortic punch instrument.

FIG. 5B shows a surgeon or surgeon's assistant applying proximal finger pressure to the opening made by the instrument of FIG. 5A to minimize blood loss through the opening prior to insertion of the intravascular hemostasis device of FIG. 1 into the vessel.

FIG. 6 is a perspective view of an alternative embodiment of an intravascular hemostasis device constructed in accordance with the principles of the present invention in which the sealing member has a plurality of movably embedded wires therein which provide support to the sealing member in its expanded, sealing configuration.

FIG. 9B shows the intravascular hemostasis device of FIG. 9A following removal of the device from the blood vessel.

FIG. 10C is a side-elevational view of the distal end portion of an alternative embodiment of an intravascular hemostasis device wherein the sealing member is in the form of a spiralled wire or ribbon which can be actuated to an expanded configuration by relative axial movement of a first and second elongated tubular member.

FIG. 10D is a side-elevational view of the distal end portion of the intravascular hemostasis device of FIG. 10C showing the sealing member in its expanded configuration.

FIG. 11 shows the sealing member of FIG. 10C with a coating of polyurethane or similar material applied thereto which acts as an impermeable barrier to fluid flow.

DETAILED DESCRIPTION OF THE PREFERRED EMBODIMENTS

Figure 1:
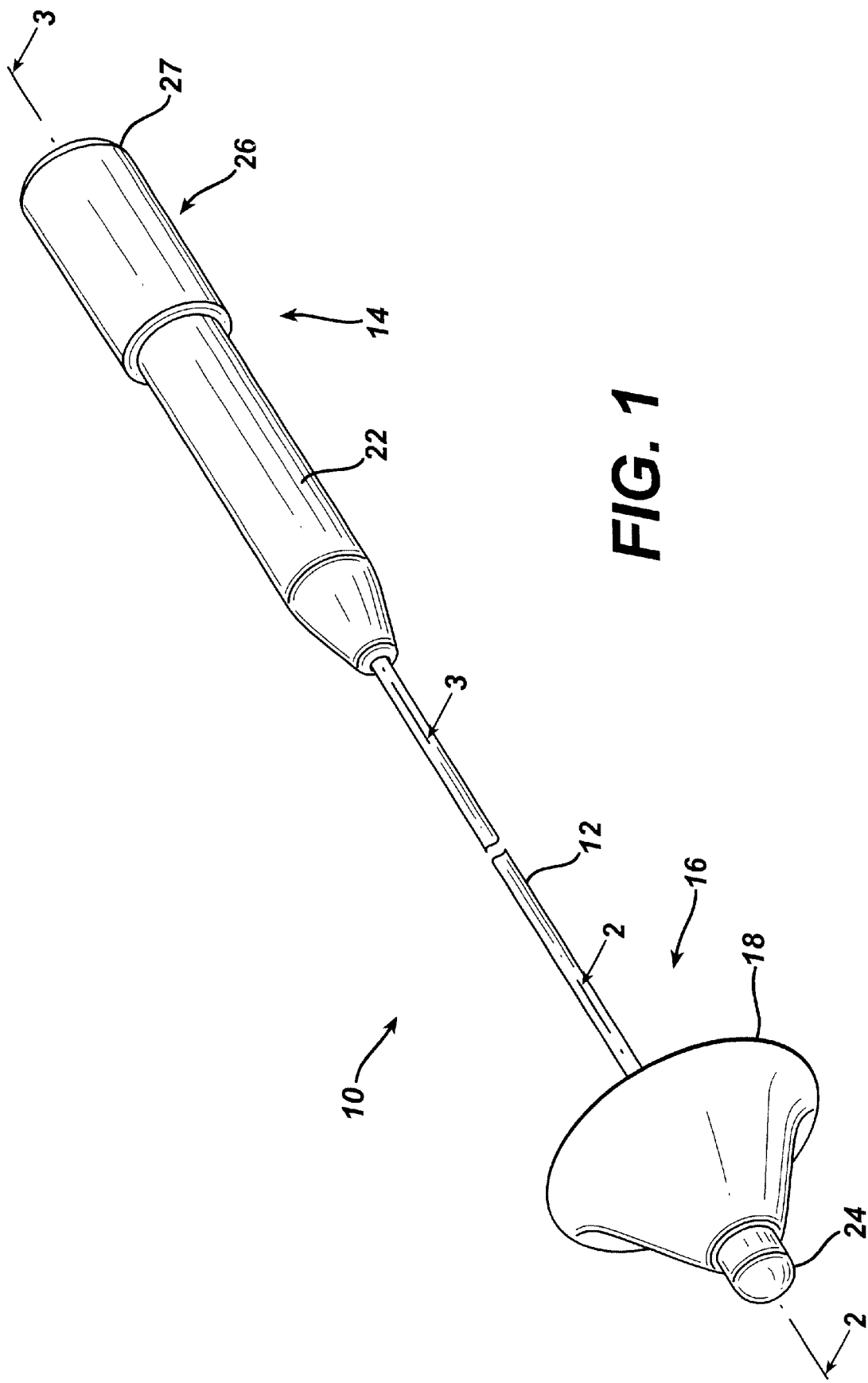
FIG. 1 is a perspective view of an intravascular hemostasis device constructed in accordance with the principles of the present invention.

Referring now to the drawings, and first to FIG. 1, an intravascular hemostasis device constructed according to the principles of the present invention is shown and generally indicated with reference numeral 10. The intravascular hemostasis device 10 is used to substantially seal an opening in a blood vessel, such as the aorta, while still permitting the flow of blood through the vessel. For example, the present invention is particularly well-suited to substantially seal an aortotomy incision in the aorta during the performance of a proximal anastomos procedure in which a free end of graft vessel, such as the saphenous vein, is attached to the aorta. The present invention thus avoids the necessity of using a clamp, such as a side-biting clamp, to seal a portion of the aorta near the aortotomy incision during the procedure. The intravascular hemostasis device 10 may also be used in sealing various other vessels or arteries or organs in the body where an opening needs to be made during the performance of a medical or surgical procedure.

For consistency and convenience, throughout the description the two end sections of the intravascular hemostasis apparatus are referred to as the proximal and distal end portions respectively, the distal end portion of the device being the end which is inserted (at least partially) into the selected vessel within the patient and the proximal end portion being the opposite end of the device which is closest to the user of the device.

According to a first aspect of the present invention, the intravascular hemostasis device 10 generally comprises at least a first elongated tubular member 12 which has a proximal end portion 14 and a distal end portion 16, and a flexible, deformable sealing member 18 coupled adjacent to the distal end portion 16 of the elongated tubular member 12. The sealing member 18 is preferably injection molded to the tubular member 12 using conventional injection molding techniques known to the person of ordinary skill in the art. To enhance the bonding strength of the bond between the sealing member 18 and the tubular member 12, a primer material such as polyolefin can be added to the outer surface of the tubular member 12 or the outer surface roughened, a binding material such as a polyester material (e.g., Dacron) can be added to the material forming the sealing member (e.g., silicon) in its fluid form (e.g., prior to being injection molded and cured), or the surface area of the shoulder portion 21 (described below) of the sealing member 18 can be increased to increase the total bond surface area. Additionally, as a potential security measure to prevent the sealing member 18 from inadvertently breaking free of the tubular member 12 and becoming dislodged in the blood vessel, a wire, for example, can be inserted into the mold and partially embedded in the sealing member 18 to act as a safety "leash" in the event of inadvertent bond failure.

FIGS. 2 and 4 illustrate in detail the configuration of the sealing member 18. The sealing member 18 has a generally cup-shaped, or umbrella-like, configuration in its natural pre-formed expanded state and is made from a biocompatible, radially compressible material such as silicone. By "radially compressible," it is meant that the sealing member 18 is generally uniformly radially transformable between a free, pre-formed expanded state and one or more compressed, compacted states in which the sealing member 18 has a smaller cross-sectional diameter than in its natural expanded state. The sealing member 18 has a circumferential rim portion 19 which is adapted to substantially form a seal against an inner wall of a blood vessel, such as the aorta, around an opening therein to create a region of hemostasis as will be described in greater detail below. The sealing member 18 is radially self-expandable. By "self-expandable," it is meant that the sealing member 18 is biased to its expanded state (i.e., it will naturally tend to migrate back towards its natural, pre-formed expanded state from its compressed state).

The circumferential rim portion 19 of the sealing member 18, which is adapted to seal against an internal wall of the blood vessel, preferably has less material thickness than the remaining body portion of the sealing member 18 as shown in FIG. 4. The thinner, more flexible portion of the sealing member 18 at its circumferential rim portion 19 allows the sealing member 18 to flex at its outer periphery to allow the sealing member to more substantially sealingly engage with the annular portion of the interior of the blood vessel about the opening therein to thereby enhance the sealing capability of the device. The thinner rim portion 19 of the sealing member 18 also allows the rim portion 19 to more easily flex to conform to uneven surfaces on the interior of the blood vessel, such as those created by the presence of plaque and other atherosclerotic luminal wall surface materials. The sealing member 18 also includes an annular shoulder, or elbow, portion 21, located at the opposite end of the sealing member to the circumferential rim portion 19. The undersurface of shoulder portion 21 may be substantially flat as shown in the drawings to provide a relatively large surface area for engaging the sealing member 18 with the support hub 24 (described below). The support hub 24 provides enhanced support to the sealing member 18 in its expanded, sealing configuration and substantially resists movement of the sealing member 18 to its inverted configuration as will be described in greater detail below.

The sealing member 18 is preferably made from a molded compliant biocompatible material, such as silicone, which has the requisite flexibility to be radially compressible from an expanded state to a compressed state for ease of insertion of the sealing member into a blood vessel through an incision therein. Optimally, the sealing member 18 will be made from a material, or have a material coating added thereto, that provides material properties and dimensions to the sealing member 18 that provide stiffness, strength, density, hardness, torsional and lateral deflection resistance, and any other property necessary to substantially resist perforation from contact by suture needles or the like when the sealing member is in its expanded state within the vessel.

The sealing member 18 can also be made from various other biocompatible materials that have the requisite flexibility and compressibility required for operation of the device, such as polyurethane, polycarbonate, and other suitable biocompatible materials that will adequately serve to perform the above-mentioned duties. The sealing member 18 preferably has an outer cross-sectional diameter at its rim portion 19 which is sized to sufficiently seal an opening in a blood vessel, such as the aorta, made by a conventional aortic circular punch instrument, for example. For example, the cross-sectional diameter of the rim portion 19 of the sealing member 18 should be at least two times the diameter of the opening in the vessel, for example about three times the diameter of the opening, and more preferably about four times the diameter of the opening. Non-limiting ranges for the cross-sectional diameter of the rim portion 19 of the sealing member 18 will vary from between about 4 and 20 mm, for example between about 8 and 15 mm, depending on the size of the particular vessel and the diameter of the opening in the vessel.

Advantageously, the sealing member 18 is moveable to an inverted configuration to facilitate its removal from a blood vessel in which the sealing member 18 has a second expanded state which is a mirror image of its first expanded state when a sufficient force is applied to the sealing member as will be described in more detail below in connection with FIGS. 5A–M. For example, the sealing member 18 is configured such that when a sufficient force is applied to the sealing member 18 by the inner wall of the blood vessel as the elongated tubular member 12 is moved away (e.g., proximally) from the blood vessel, the sealing member 18 will invert to its inverted configuration. The sealing member 18 is at least partially radially compressible from its second expanded state to a second compressed state to allow for removal of the sealing member 18 from the blood vessel through the opening in the blood vessel.

Turning now to FIG. 3, the intravascular hemostasis device 10 further includes a handle 22 coupled to the proximal end portion 14 of the device which is adapted to be grasped by the surgeon or surgeon's assistant during operation of the device. In a preferred embodiment, the device includes a support element to provide enhanced rigidity to the sealing member 18 when in its expanded state to prevent the sealing member from inadvertently inverting to its inverted configuration during use of the device and to provide enhanced rigidity to the sealing member to enhance its sealing function. For example, as illustrated in FIGS. 1 and 2, the device 10 includes a support hub 24 at the distal end of the device which is located immediately adjacent to the shoulder portion 21 of sealing member 18 under the control of at least one spring 30 (see FIG. 3). The support hub 24 is spring-biased into contact with the shoulder portion 21 of sealing member 18 in its natural state and acts as a support surface to support the sealing member 18 in its expanded state and to substantially prevent the sealing member 18 from inadvertently moving to its inverted configuration.

The support hub 24 is moveable axially away from the sealing member (i.e., distally) to facilitate inversion of the sealing member 18 and removal of the sealing member 18 from the blood vessel. To accomplish this movement, as shown in FIG. 3, the support hub 24 is fixed to an actuator 26 which is operatively coupled to the handle 22. Actuator 26 includes a translatable wire or hypotube 28 which is slidably retained within the handle 22 and the elongated tubular body 12 and which is fixedly coupled to a finger-actuated actuator button 27. The hypotube 28 may be made from any suitable durable material such as stainless steel and the like. A spring 30 is located within the handle 22 between inner support 31 of the handle 22 and an inner surface 33 of button 27, to bias the actuator button 27 into its natural retracted, closed configuration in which the support hub 24 engages the shoulder portion 21 of sealing member 18 as shown in FIG. 2. Actuation of actuator 26 (e.g., by grasping handle 22 and pushing on actuator button 27) will cause support hub 24 to move axially away from sealing member 18 which will remove support from the shoulder portion 21 of sealing member 18 and facilitate inversion of the sealing member as will be described below in connection with FIGS. 5A–M.

The operation of the device 10 will now be described with reference to FIGS. 5A–M. In the following description, the device 10 is used seal a region around an opening in the aorta to facilitate attaching a coronary bypass graft, such as a saphenous vein, to the aorta. It is contemplated, however, that the device 10 may be used in a variety of other medical and surgical procedures involving incisions or openings in blood vessels, organs and the like.

Conventional coronary bypass graft procedures require that a source of arterial blood be prepared for subsequent bypass connection to the diseased artery. An arterial graft can be used to provide a source of blood flow, or a free vessel graft may be used and connected at the proximal end to a source of blood flow. Preferably, the source of blood flow is any one of a number of existing arteries that are dissected in preparation for the bypass graft procedure. In many instances, it is preferred to use either the left or right internal mammary artery. In multiple bypass procedures, it may be necessary to use free vein graft vessels such as the saphenous vein of the leg or the cephalic or basilic veins in the arm. Alternatively, free arterial grafts can be used when the leg or arm veins are unavailable or are unsuitable, such as the gastroepiploic artery in the abdomen, and other arteries harvested from the patient's body. Synthetic graft materials, such as Dacron or Gortex grafts, can be used as well. If a free graft vessel is used, the upstream end (proximal) of the dissected vessel, which is the arterial blood source, will be secured to the aorta to provide the desired bypass blood flow in a proximal anastomosis procedure, and the downstream end (distal) of the dissected vessel will be connected to the target vessel in a distal anastomosis.

Where a free graft vessel is used as the bypass conduit, the patient is prepared for surgery according to known techniques for conventional open chest surgery where access is gained to the aorta by a partial or median sternotomy. Preferably, the anastomosis of the free graft vessel is performed without placing the patient on cardiopulmonary bypass and after the construction of the distal anastomosis to the coronary artery. Alternatively, some surgeons will prefer to perform the proximal anastomosis as the initial step to ensure aortic blood flow to the graft. Preferably, CPB and aortic cross-clamping are avoided by using pharmacologic cardiac stabilization such as described in the Background section and in the co-pending patent application for "Compositions, Apparatus and Methods For Facilitating Surgical Procedures," Ser. No. 09/131,075, filed Aug. 7, 1998 and invented by Francis G. Duhaylongsod, M.D, the entire contents of which are expressly incorporated by reference herein. Such pharmacologic stabilization can be used to stabilize the heart to facilitate the distal and/or proximal anastomosis procedures. Other pharmacological or mechanical methods of cardiac stabilization may also be used. The aorta may also be accessed by a smaller incision such as a mini-thoracotomy incision between the ribs or by a portal access procedure through one or more ports in the chest wall.

In this example, the heart is exposed and access to the aorta 50 is achieved following a median stesootomy. With the heart so exposed, a slit 52 approximately 1–5 mm in length is formed in a side wall of the aorta 50 at a proximal anastomosis site with a scalpel or other appropriate surgical cutting instrument, such as that disclosed in co-pending pending patent application Ser. No. 09/124,534 for "Surgical Cutting Instrument and Method of Use," filed Jul. 29, 1998, and invented by Michael Hogendijk. Alternatively, a circular or oval aortic punch 57 may be used to facilitate the aortotomy as shown in FIG. 5A After incision of the aorta, temporary control of vessel bleeding is obtained by applying proximal finger pressure over the aorta until the device 10 is inserted therein as shown in FIG. 5B.

Figure 5C:
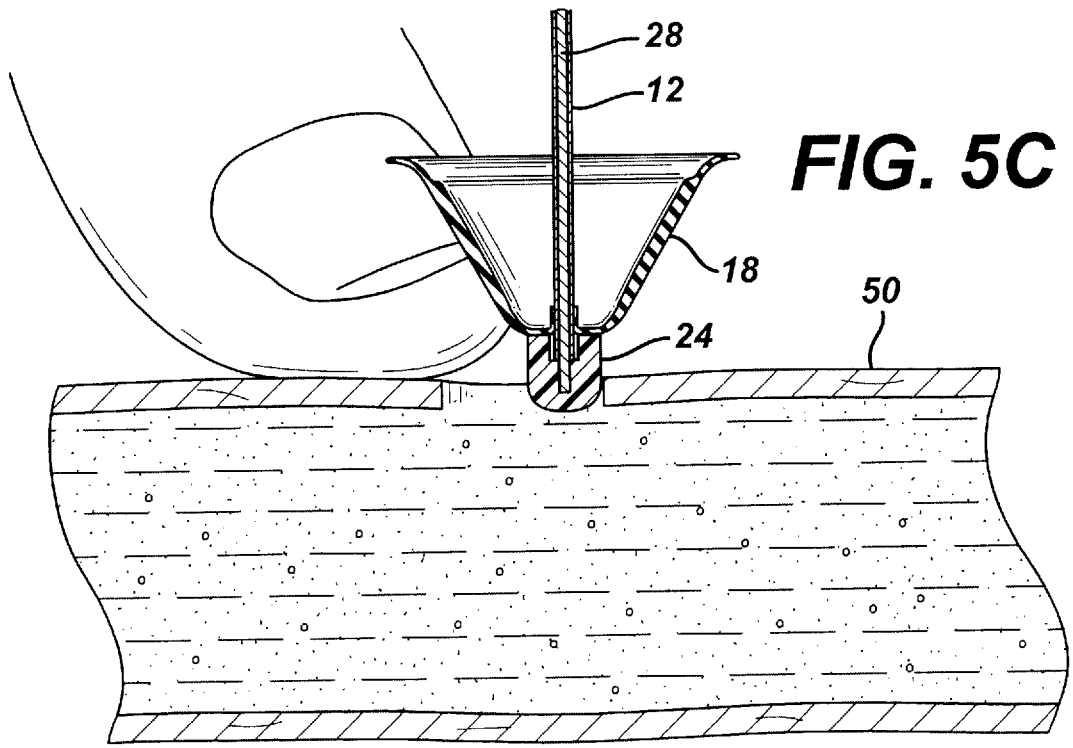
FIG. 5C shows the intravascular hemostasis device of FIG. 1 being inserted into the opening in the aorta of FIG. 5B.
Figure 5D:
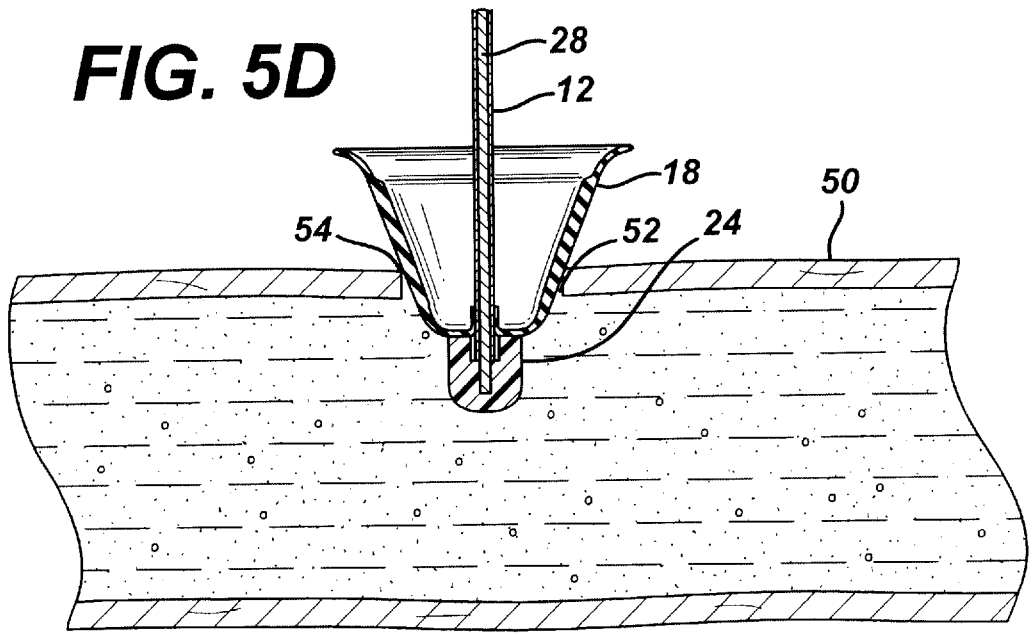
FIG. 5D illustrates the insertion of the intravascular hemostasis device into the opening in the aorta and shows the sealing member being compressed from its preformed expanded state to a compressed configuration for insertion through the opening.
Figure 5E:
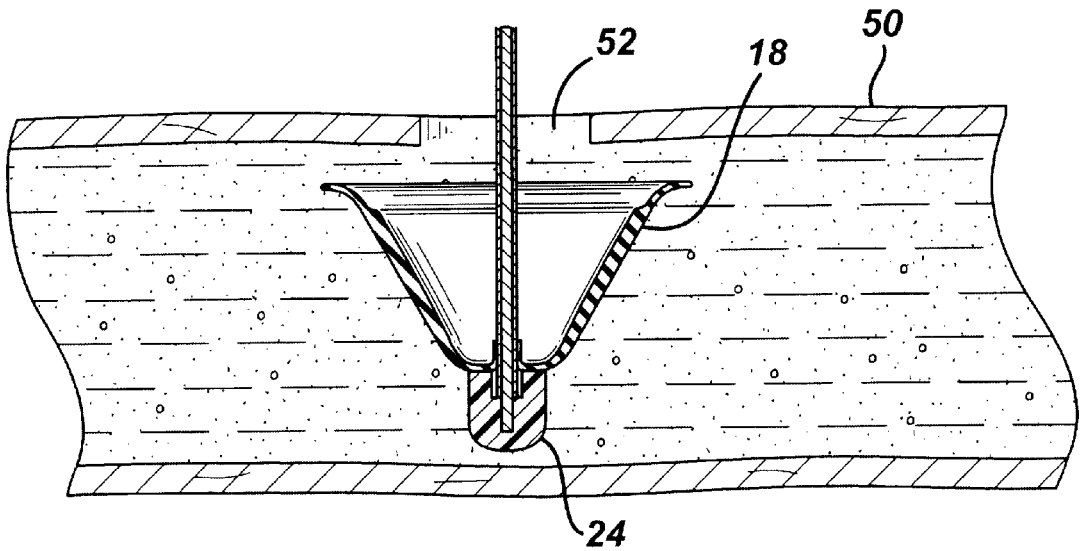
FIG. 5E illustrates the intravascular hemostasis device of FIG. 1 after the sealing member has been fully inserted into the aorta through the opening therein and has resumed its natural expanded configuration within the blood vessel.
Figure 5F:
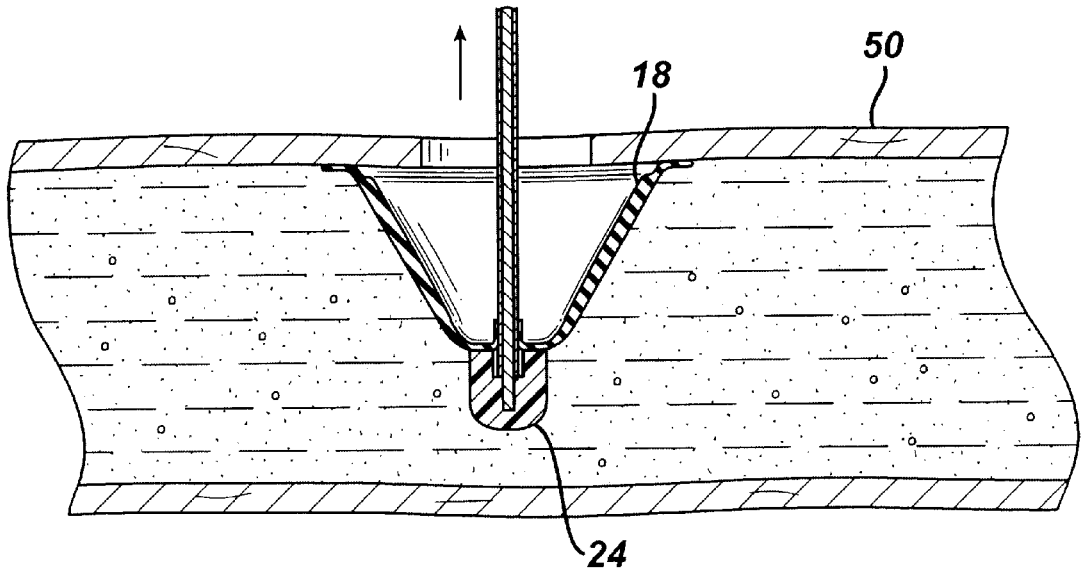
FIG. 5F shows the sealing member of FIG. 5E in its sealing configuration within the aorta whereby it substantially occludes the flow of blood through the opening therein.

The sealing member 18 in its expanded configuration is then inserted into the aorta 50 through the small incision 52 as illustrated in FIG. 5C. As the sealing member 18 passes through the opening in the aorta, the annular aortic wall region 54 about opening 52 exerts a radially-inward directed force to the sealing member 18 which causes the sealing member 18 to radially compress to assume its compressed configuration as shown in FIG. 5D. This allows the sealing member 18 to be easily placed within the aorta 50. Once the sealing member 18 is fully inserted within the aorta 50, the sealing member 18 will naturally migrate and radially expand back towards its natural expanded cup-like configuration as shown in FIG. 5E. Next, the surgeon or the surgeon's assistant applies proximally directed tension to the handle 22 to engage the annular rim portion 19 to the inner wall 54 of the aorta 50 as illustrated in FIG. 5F. A substantially blood-free zone is thus created around the opening 52. The device only occludes substantially the area of the aorta around the opening 52 and does not substantially interfere with the blood flowing through the aorta.

Figure 5G:
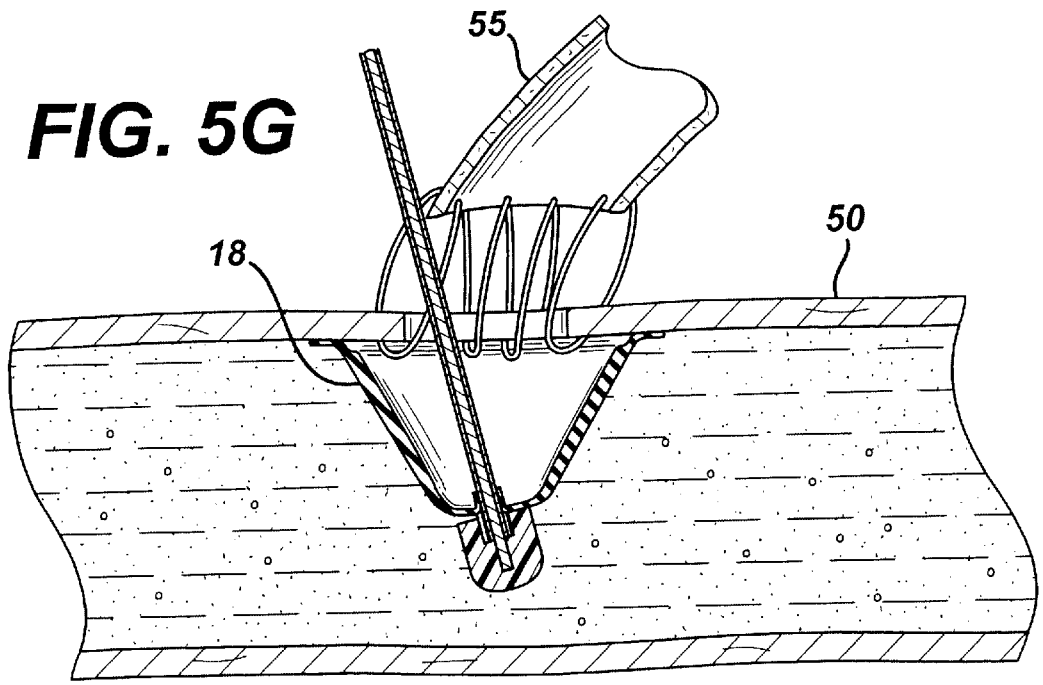
FIG. 5G illustrates a plurality of purse string sutures being attached to the bypass graft vessel and the aorta with the sealing member inside the aorta.
Figure 5H:
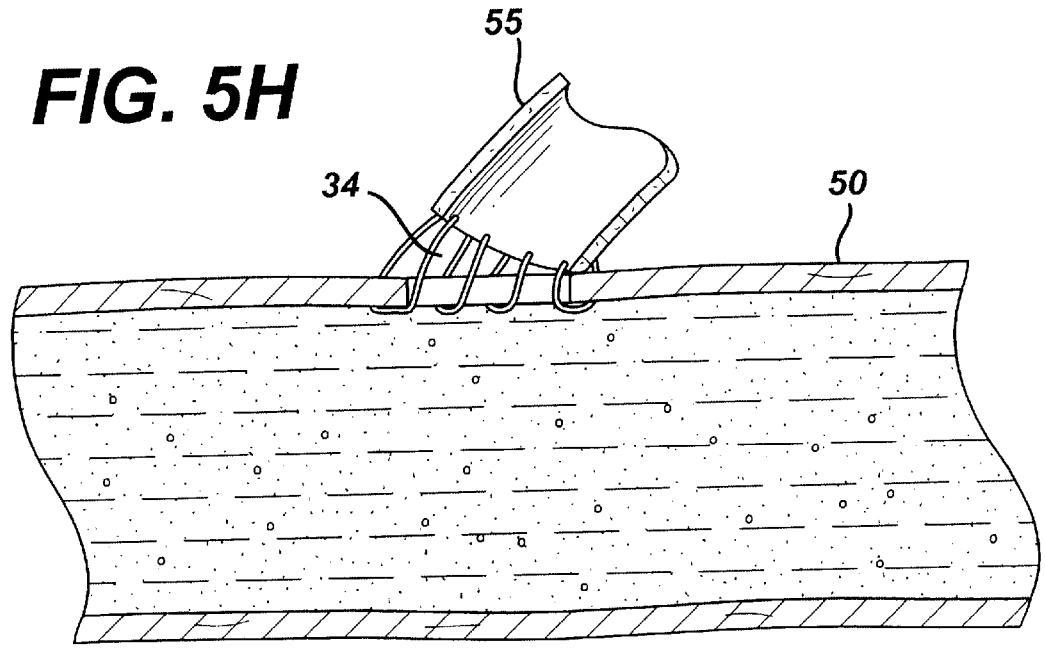
FIG. 5H illustrates how a surgeon or surgeon's assistant pulls the ends of the purse string sutures of FIG. 5G to bring the bypass graft vessel to the aorta while leaving a sufficient space between the bypass graft vessel and the aorta to facilitate removal of the sealing member (which is not shown in the drawing for clarity).

Once the seal has been created around the opening in the aorta 50, the surgeon or surgeon's assistant then loosely places about five suture loops of 5/0 polypropylene around the "heel" of the graft vessel 55 (e.g., a saphenous vein) and passes the sutures through the aortic wall as illustrated in FIG. 5G. The suture loops are pulled up to approximate the graft vessel 55 to the aorta 50 while leaving a sufficient space 34 between the vessels to allow for removal of the device from the aorta as shown in FIG. 5H (the device 10 is not shown in FIG. 5H for clarity). For a more complete description of a typical proximal anastomosis procedure, for example, the reader is referred to Doty, R. B. M.D., "CARDIAC SURGERY Operative Technique," Ed. Mosby-Year Book, Inc., 1997, pp. 282–289, the entire contents of which are incorporated by reference herein.

Figure 5I:
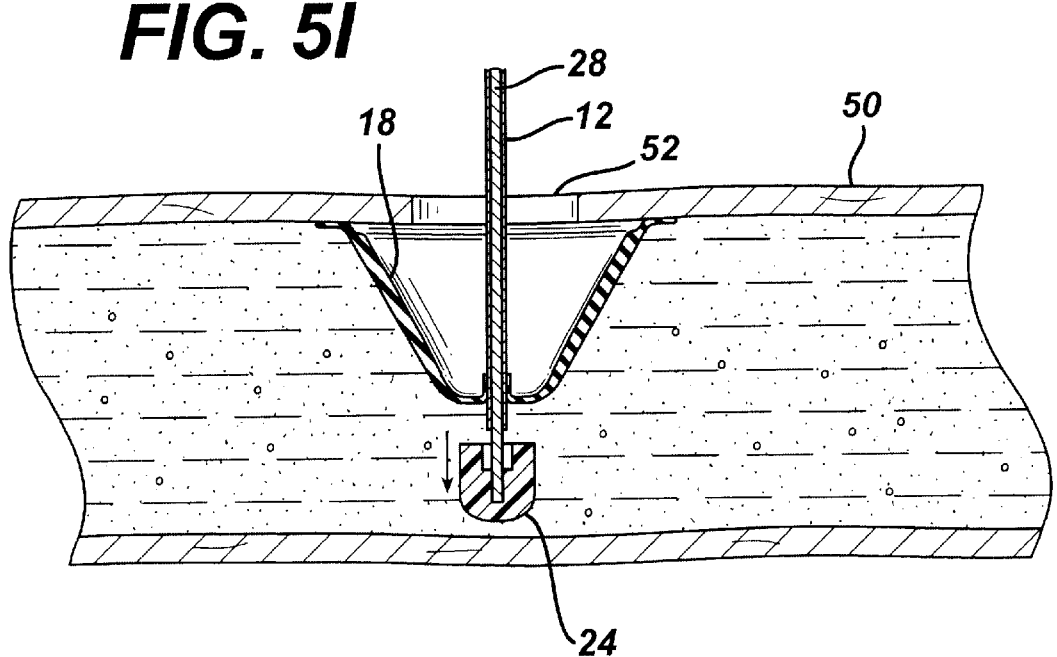
FIG. 5I illustrates the axial movement of the support hub away from the sealing member to facilitate inversion of the sealing member into a second expanded configuration which is a mirror image of its first, pre-formed expanded configuration.
Figure 5J:
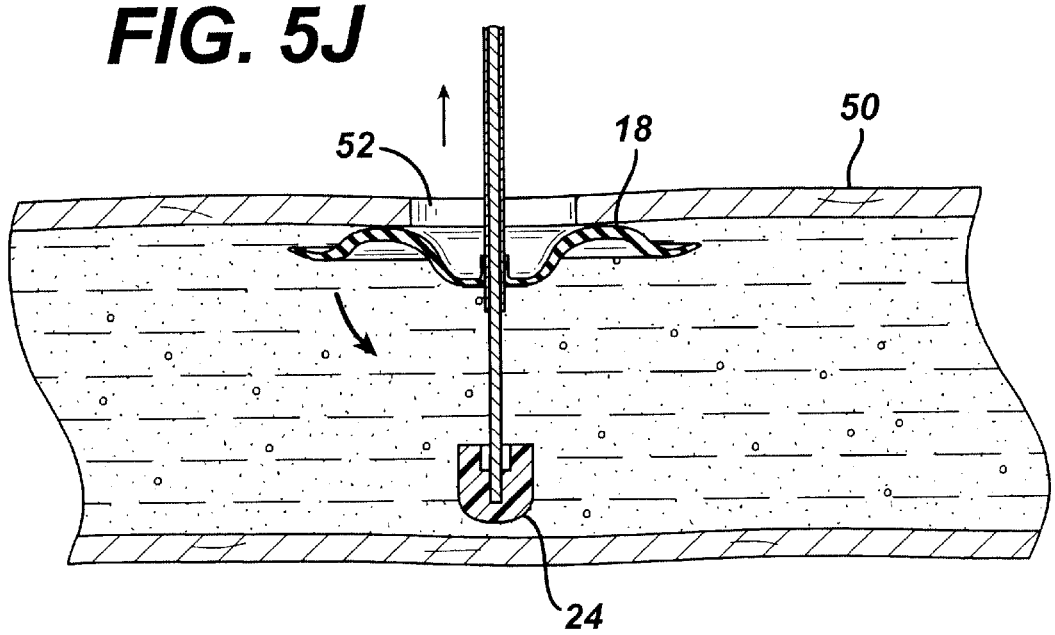
FIG. 5J shows the sealing member of FIG. 5I moving into its inverted configuration.
Figure 5K:
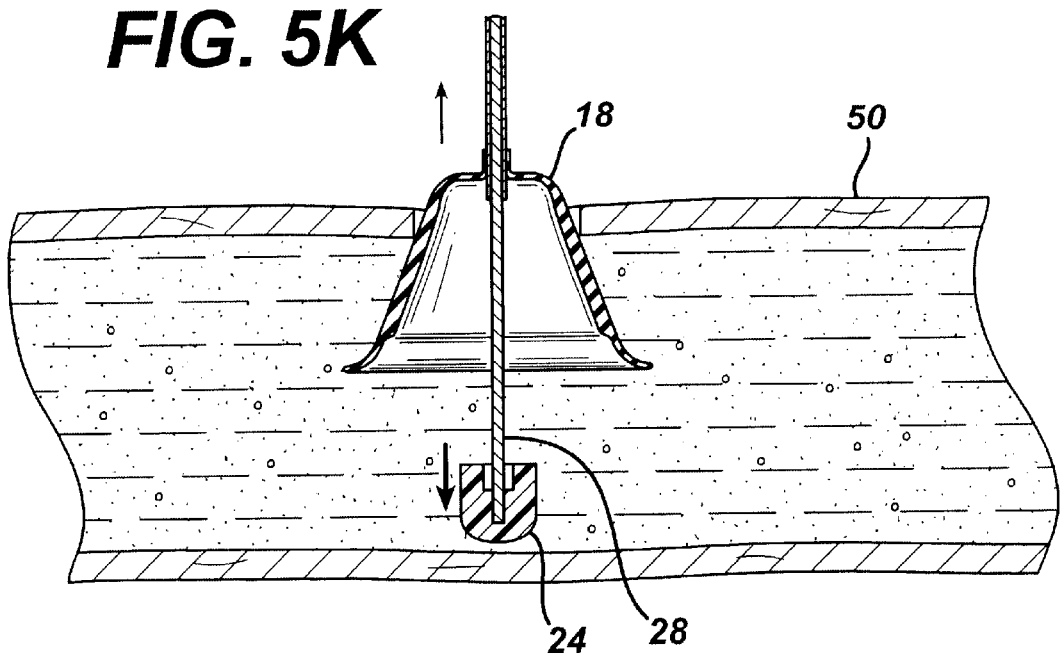
FIG. 5K shows the sealing member of FIG. 5J in its inverted configuration and being removed from the aorta.
Figure 5L:
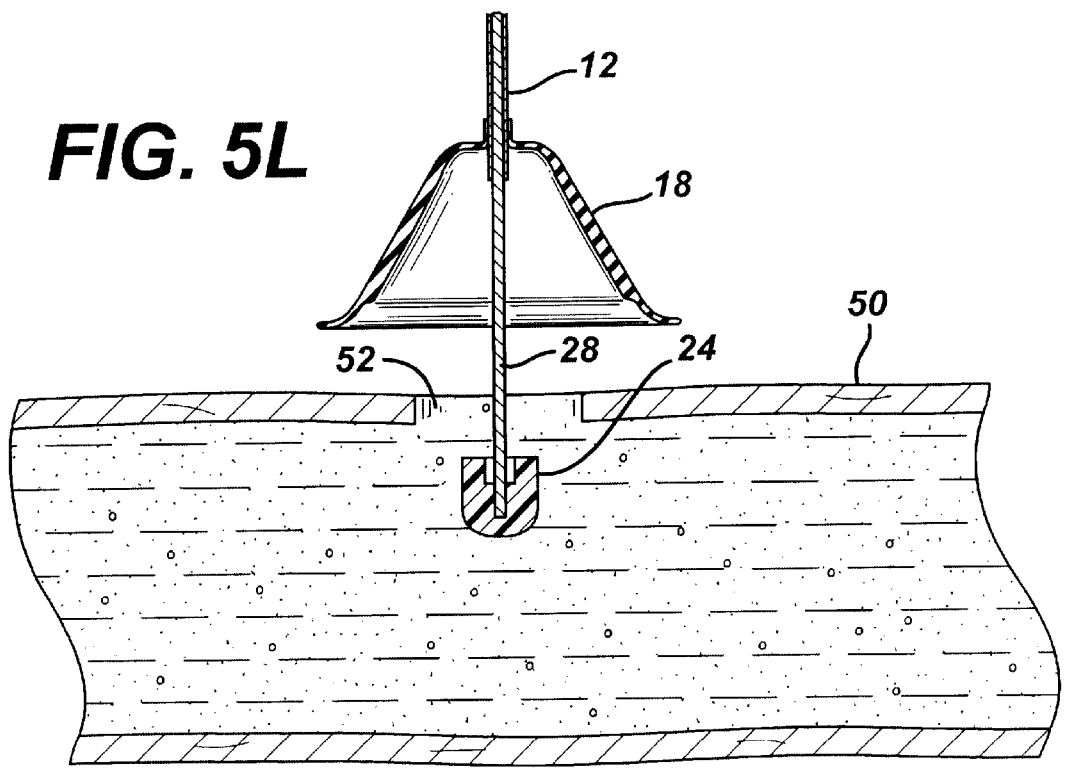
FIG. 5L shows the sealing member of FIG. 5K following its removal from the vessel.
Figure 5M:
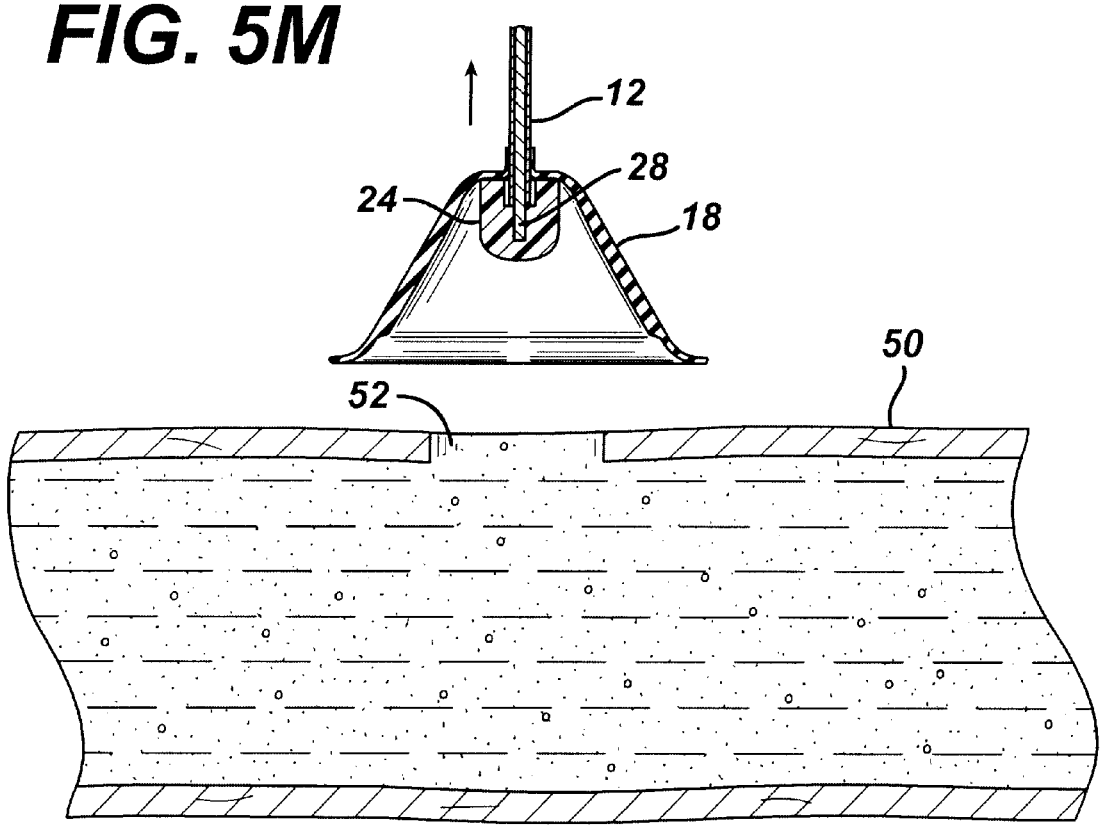
FIG. 5M shows the final configuration of the sealing member of FIG. 5L following removal of the device from the aorta.

Once the sutures are in place and the surgeon is ready to remove the device 10 from the aorta 50, the surgeon or surgeon's assistant applies pressure on actuator button 27 which causes support hub 24 to move axially (e.g., distally) away from the shoulder portion 21 of sealing member 18 as illustrated in FIG. 5I (the graft vessel 55 is not illustrated in drawing FIGS. 5I–M for clarity and convenience). The separation of the support structure from the sealing member 18 facilitates inversion of the sealing member 18 from its first expanded, sealing configuration to a second expanded configuration which is a mirror image of the first expanded configuration. For example, as the surgeon or surgeon's assistant moves the elongated tubular body 12 proximally away from the aorta 50 (e.g., by grasping handle 22), the interior wall of the aorta 50 adjacent the rim portion 19 of the sealing member 18 applies a sufficient force to the sealing member 18 to cause it to move towards its inverted configuration as shown in FIG. 5J. The sealing member 18 in its inverted configuration is then at least partially radially compressible from its second expanded state to a second compressed state to allow for removal of the sealing member 18 from the aorta 50 through the opening 52 in the aorta as illustrated in FIGS. 5K. The surgeon or surgeon's assistant then removes the sealing member 18 from the aorta 50 around the loose sutures (FIGS. 5L and 5M) and pulls the sutures tightly around the graft to give the graft a patent seal. As noted above, the distal anastomosis procedure to the coronary artery can be accomplished before, during, or after the proximal anastomosis. The anastomosis procedure is completed using conventional techniques.

Figure 7:
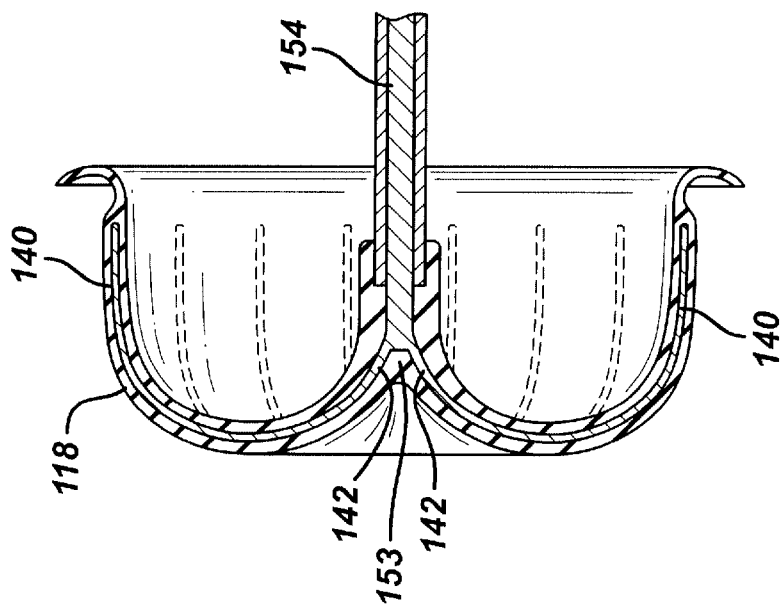
FIG. 7 is a cross-sectional view of the distal end portion of the intravascular hemostasis device of FIG. 6.

An alternative embodiment of the present invention will now be described with reference to FIGS. 6–9. In this particular embodiment, the intravascular hemostasis device includes a different support mechanism for providing rigidity to the sealing member in its expanded state in lieu of the support hub 24 configuration of FIGS. 1–5. As illustrated in FIGS. 6 and 7, the support hub 24 structure and its corresponding actuating mechanism are replaced by a plurality of movably embedded wires which are circumferentially spaced around the sealing member. Specifically, intravascular hemostasis device 110 includes a plurality of thin wires 140 (see FIG. 7) which preferably are equally spaced circumferentially around the sealing member 118. The wires 140 serve to add rigidity and strength to the sealing member 118 while in its expanded state and to substantially restrict movement of the sealing member 118 into its inverted configuration during operation of the device 110.

As shown in FIG. 7, the proximal ends 142 of the wires 140 are secured to the distal end 153 of an inner elongated tubular portion 154 which extends from a cap 152 which is rotatably coupled to standard luer fitting member 150 (such as is commercially manufactured by Qosina Corporation (Edgewood, N.Y.)) by an appropriate method, such as heat shrink Teflon™ tubing that is placed over the wires and shrunk in place to the distal end 153 of the tubular portion 154. The proximal ends 142 of the wires 140 could also be secured to tubular portion 154 through the use of a band integrally formed to the tubular portion or by use of an adhesive. The luer fitting member 150 includes a pair of fins 151 which can be grasped by the user of the device to facilitate manipulation of the cap 152 and removal of the wires 140 from the sealing member 118 as is described below.

The wires 140 are preferably made or coated with a material which does not cause an adverse reaction when placed in the patient's body. Suitable materials include stainless steel, titanium, Nitinol, some plastics such as nylon, some composite materials, and Teflon™-coated wires, including Teflon™-coated stainless steel. Preferably, the wires 140 are made from Nitinol and are heat treated in a pre-formed shape conforming generally to the cup-shaped configuration of the sealing member 118 as shown in FIG. 7. In an alternative embodiment, the wires 140 can extend along the length of the device 110 from its distal end portion 116 to its proximal end portion 114 through a plurality of guideways (not shown). The guideways would serve to protect the wires 140 while also maintaining proper positioning of the individual wires. The guideways and wires 140 can be extruded as an integral part of tubular member 112, or alternatively are extruded individually and are later inserted into the tubular member 112. Where the guideways are used, the cap 152 could include a significantly shorter hub portion extending therefrom to which the proximal ends of the wires would be secured.

In the embodiment shown, several wires 140 are used, although a lesser number of wires, such as between four to eight wires, could be used, depending on the application of the device 110. The cap 152 can be secured to luer fitting 150 in a number of ways such as by an interference or press-fit relationship. Alternatively, for example, in the embodiment shown in FIG. 8, the cap 152 includes a single thread 156 (although more than one thread could be used) on an inside surface of the cap 152 which mates with a corresponding thread 158 on an outside surface of a proximal portion of the luer fitting 150. Accordingly, an approximately one-half step clockwise rotation of cap 152 relative to luer fitting 150 allows removal of the cap 152 from the luer fitting 150. The cap 152 can then be drawn proximally away from the luer fitting 150 to cause wires 140 to be withdrawn from sealing member 118 as will be described below in connection with FIGS. 9A and 9B. As shown in FIG. 8A, the cap 152' could also include a plurality of threads 156' which are configured to mate with a corresponding thread 158' of luer fitting 150'. In the embodiment of FIG. 8A, the tubular body 154' is not directly fixed to cap 152'. Instead, the tubular body 154' extends through and is fixedly attached to a bearing member 160 in the form of a ball bearing which is located between the cap 152' and the tubular body 154'. The bearing member 160 is freely slidable (i.e., rotatable) within the cap 152'. In this way, the bearing member 160 ensures that rotational movement of the cap 152' relative to luer fitting 150' translates to axial movement of the tubular body 154'. Thus, rotational movement of cap 152' relative to luer fitting 150' translates to step-wise axial movement of tube 154' which will in turn cause the movably embedded wires 140 to be withdrawn from the sealing member.

Figure 8:
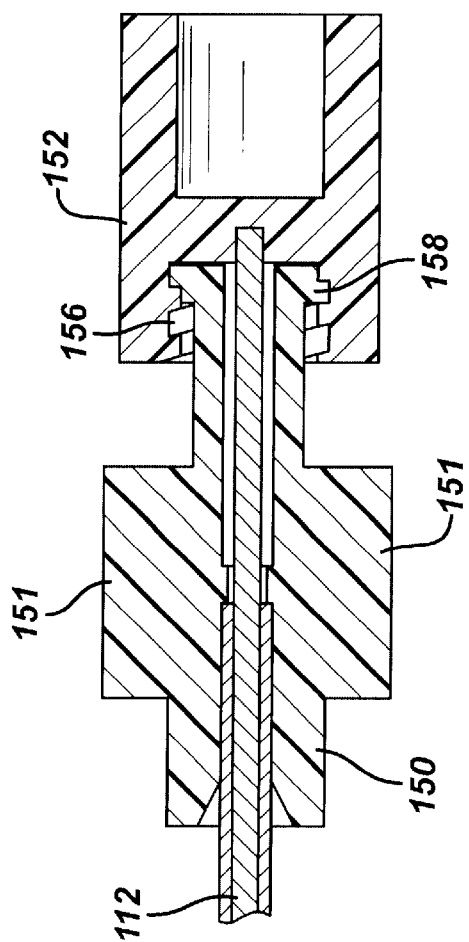
FIG. 8 is a cross-sectional view of the proximal end portion of the intravascular hemostasis device of FIG. 6.
Figure 8A:
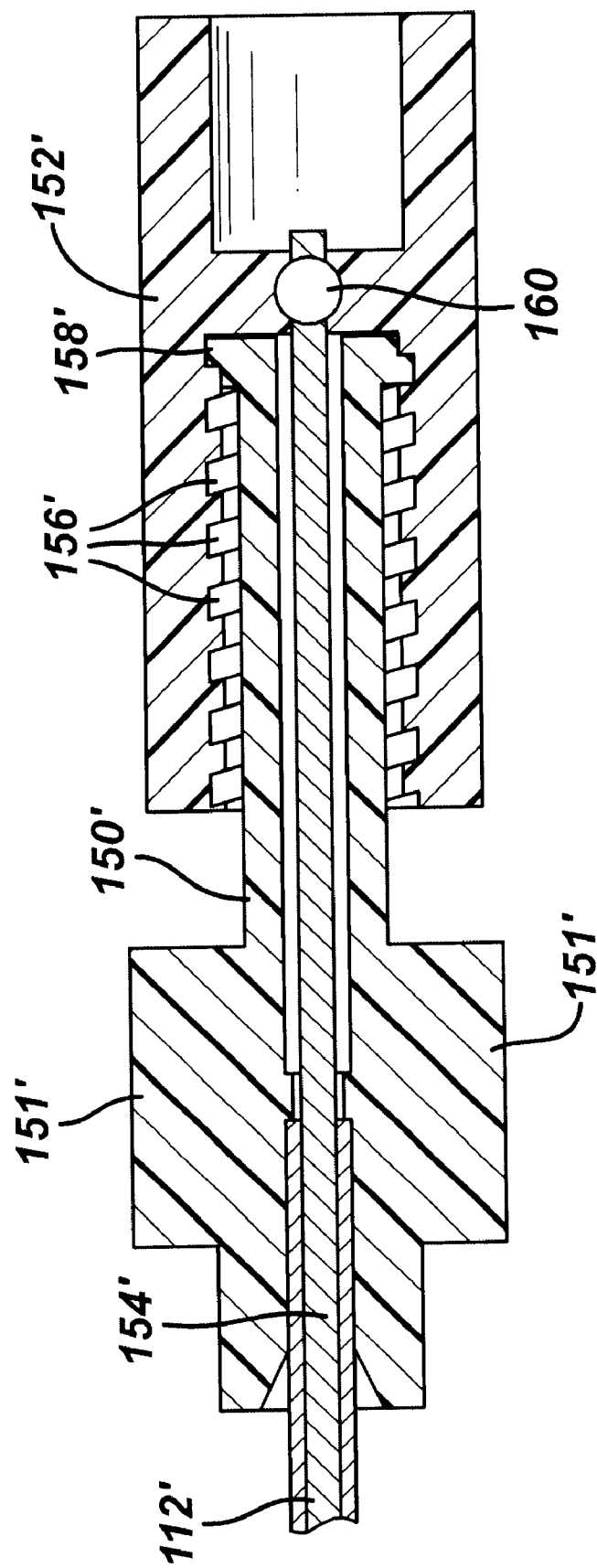
FIG. 8A is a cross-sectional view of a modified version of the proximal end portion of the intravascular hemostasis device of FIG. 6.

To operate the device 110 of FIGS. 6–8, the device 110 is inserted into a blood vessel, such as the aorta, in a similar fashion as the intravascular hemostasis device 10 of FIGS. 1–5. For example, the sealing member 118 in its expanded configuration and with the wires 140 located within the sealing member 118 is inserted into the aorta 50 through a small incision 52 as in the previous embodiment. As the sealing member 118 passes through the opening in the aorta 50, the annular aortic wall region about opening 52 exerts a radially-inward directed force to the sealing member 118 which causes the sealing member 118 to radially compress to assume a compressed configuration. This allows the sealing member 118 to be easily placed within the aorta 50. Once the sealing member 118 is fully inserted within the aorta 50, the sealing member 118 with the pre-formed wires 140 in place will naturally migrate and radially expand back towards its natural expanded cup-like configuration.

Figure 9A:
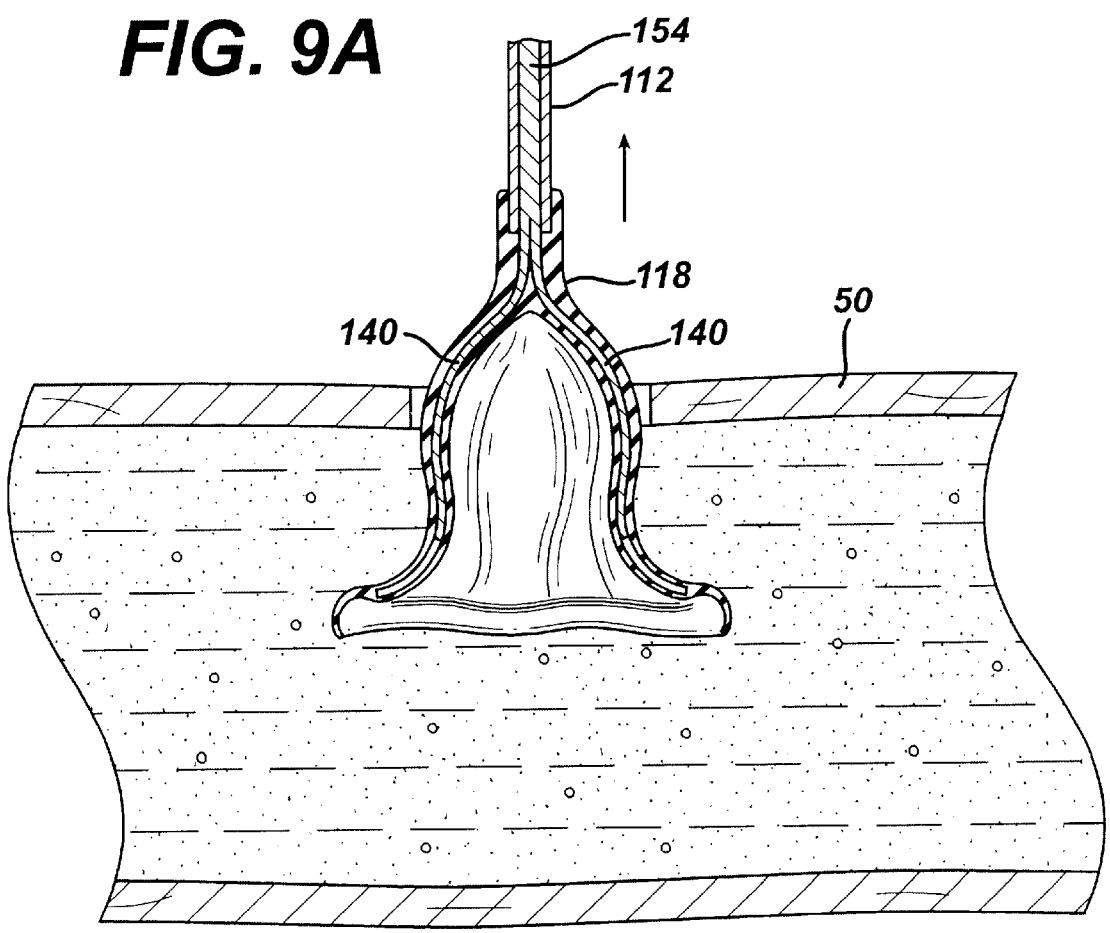
FIG. 9A is a cross-sectional view showing the intravascular hemostasis device of FIG. 6 being removed from an opening in a wall of a blood vessel with the wires partially withdrawn from the sealing member.

The sealing member 118 is removed from the blood vessel, or aorta 50, by first removing the cap 152 from the luer fitting 150 as described above (e.g., by rotating cap 152 about one-half step clockwise relative to luer fitting 150 until thread 156 disengages with the corresponding thread 158, or by rotating cap 152' relative to luer fitting 150'). Each wire 140 is then collectively withdrawn from the sealing member 118 into the tubular member 112, e.g., by drawing the cap 152 proximally away from the blood vessel (or by continuing to rotate cap 152' relative to luer fitting 150'). FIG. 9A shows the wires in the partially withdrawn position. Each wire 140 may be fully withdrawn until the wires are fully separated from the sealing member 118 and retracted into the tubular member 112 to facilitate removal of the sealing member 118. The sealing member 118 is then withdrawn from the blood vessel using a similar technique as described above in connection with FIGS. 5J–M, e.g., by having the sealing member 118 invert to an inverted configuration for ease of removal from the vessel as shown in FIG. 9B.

FIGS. 10A–D illustrate alternative embodiments of an intravascular hemostasis device constructed in accordance with the principles of the present invention. The intravascular hemostasis device 210 generally comprises a first elongated tubular member 212 and a second elongated tubular member 214 rotatably coupled (FIGS. 10A–B) or axially slidably coupled (see reference numerals 212' and 214' of FIGS. 10C–D) to the first elongated tubular member 212. A flexible sealing member 218, 218' in the form of a spirally wound ribbon or wire 219, 219' is circumscribed (e.g., spiralled) about the distal end portions of the elongated tubular members 212 and 214 (or 212' and 214') and is fixedly coupled adjacent to the distal end portions of the respective elongated tubular members 212, 214 (or 212', 214') as shown. The wire or ribbon 219, 219' is preferably made from a flexible material such as Nitinol. Alternatively, a thermoplastic material can be used. The manner of securing the wire or ribbon 219, 219' to the elongated tubular members 212, 214 (or 212', 214') can take many forms such as an adhesive, using an injection-molded PET process or a UV-cured adhesive process. As shown in FIG. 11, the entire sealing member 218 (and 218') is preferably coated with a flexible, impermeable material 220 such as polyurethane or silicone to make the sealing member impermeable to the flow of blood. Relative rotational movement between elongated tubular body members 212, 214, or relative axial movement between elongated tubular body members 212', 214', will cause the coated sealing member 218, 218' to expands towards the proximal end of the device to assume a generally cup-shaped configuration similar to the natural pre-formed cup-shaped configuration of the device 10 of FIGS. 1–5.

Figure 10A:
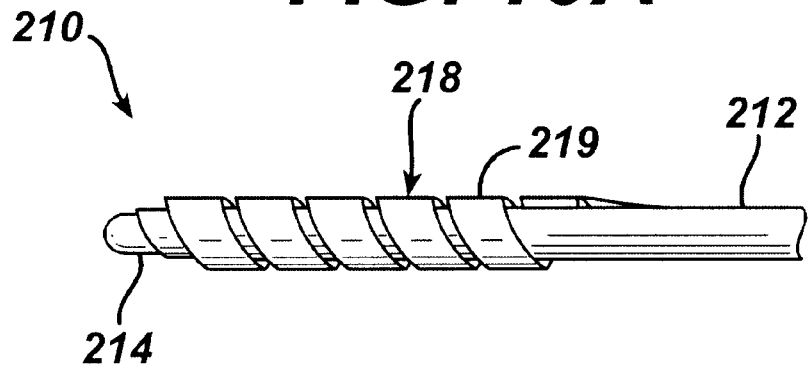
FIG. 10A is a side-elevational view of the distal end portion of an alternative embodiment of an intravascular hemostasis device wherein the sealing member is in the form of a spiralled wire or ribbon which can be actuated to an expanded configuration by relative rotational movement of a first and second elongated tubular member.
Figure 10B:
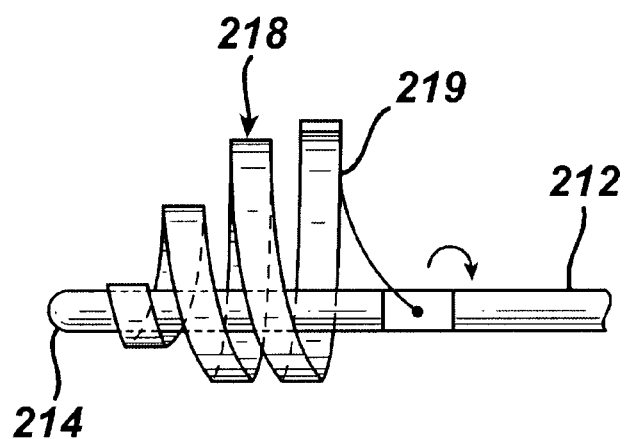
FIG. 10B is a side-elevational view of the distal end portion of the intravascular hemostasis device of FIG. 10A showing the sealing member in its expanded configuration.

To facilitate operation of the device of FIGS. 10A–B, the elongated tubular member 212 has a handle or knob (not shown) coupled thereto which can be grasped by the surgeon or surgeon's assistant. The intravascular hemostasis device can be provided with various ways to actuate the handle to position the sealing member 218 in its expanded configuration. For example, in the embodiment of FIGS. 10A–B, one possible way to accomplish rotational actuation of the handle is a thread form that is applied to an inner surface of the proximal end portion of the first elongated tubular member 212 with a mating thread on an outside surface of the second elongated tubular member 214 (similar to the thread form described in greater detail below in connection with FIG. 14) whereupon clockwise rotation of the handle results in expansion of the sealing member 218. The wire or ribbon 219 expands because it is fixed to both the first and second elongated tubular members 212, 214 adjacent its distal ends.

With respect to the embodiment of FIGS. 10C–D, relative axial movement between the first and second elongated tubular members 212', 214' could be accomplished in a number of ways. For example, a plunger-type mechanism could be used, a spring-activated sliding-push button type mechanism could be employed similar to that described above in connection with FIGS. 1–5, or a motor-driven linear actuator mechanism could be used to actuate the second elongated tubular member 214' to move axially (e.g., proximally) relative to the first elongated tubular member 212' as shown.

Those skilled in the art will appreciate that other forms of execution of the wire or ribbon 219 can be employed without departing from the scope of the present invention. For example, the sealing member may have longitudinally extending as opposed to spiralled slits. One end of the longitudinally extending slits of the sealing member will be secured to the second elongated tubular member and the other end of the longtiudinally-extending slits would be coupled to a distal end portion of the first elongated tubular member. The operation of this type of a device would be similar to that of device 210' shown in FIGS. 10C–D, e.g., radial expansion of the sealing member would occur by relative axial movement between the first and second elongated tubular members.

Figure 12A:
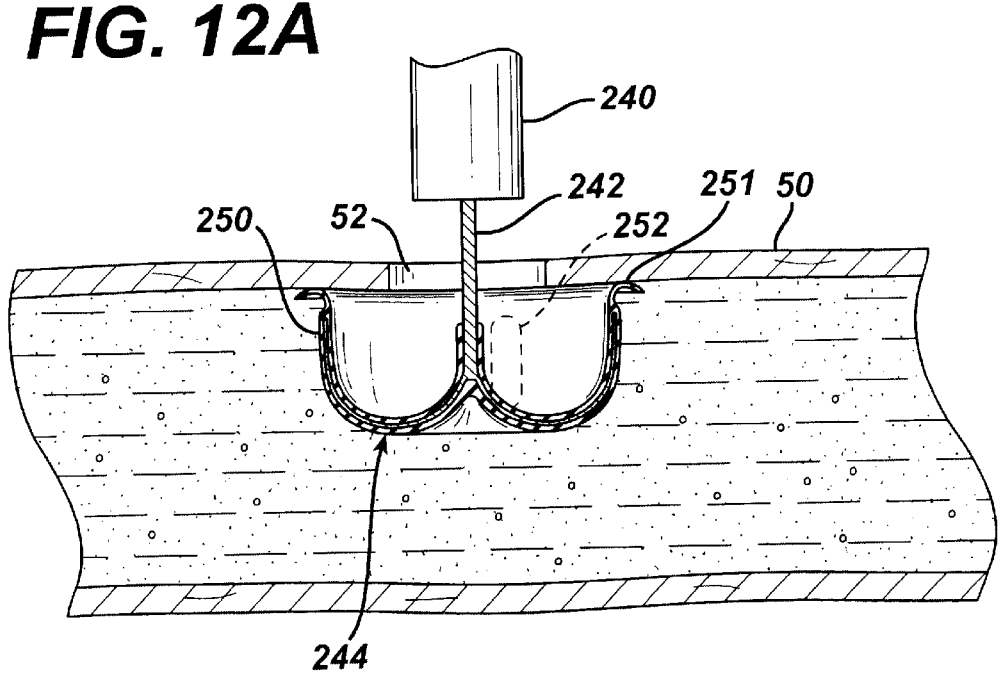
FIG. 12A is a cross-sectional view of the distal end portion of an alternative embodiment of an intravascular hemostasis device which includes a sealing member in the form of plurality of flexible wire loops in an expanded, sealing configuration within a blood vessel.
Figure 12B:
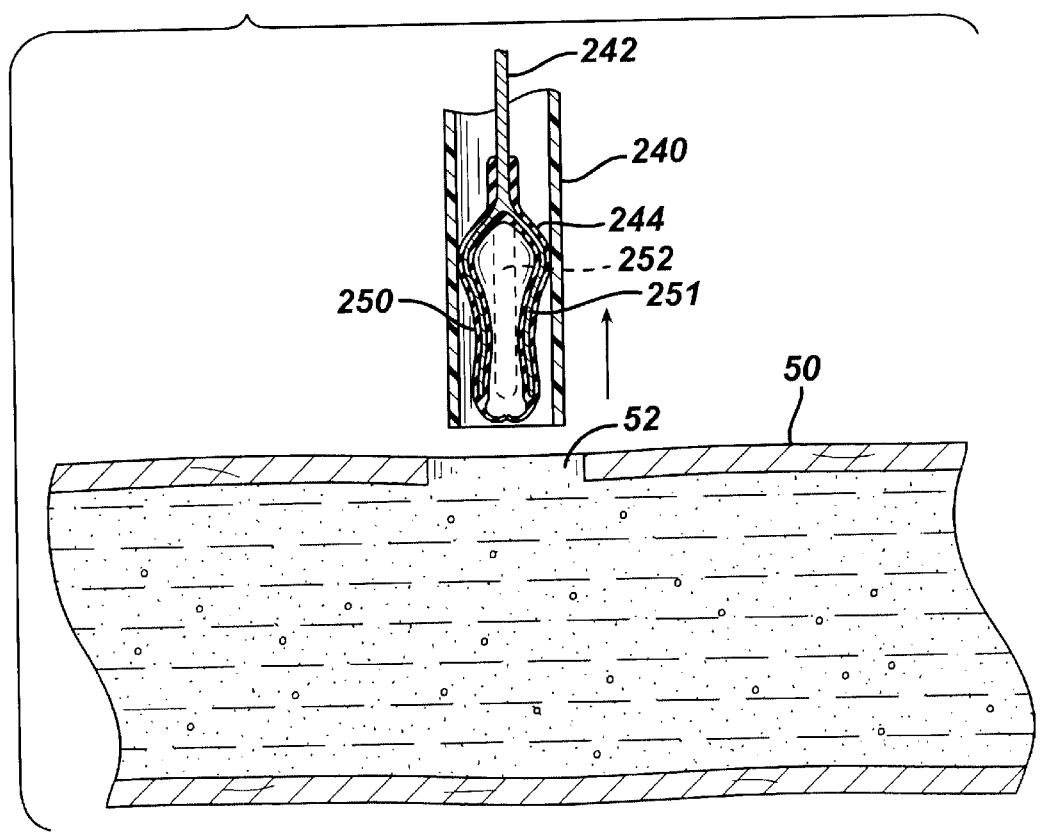
FIG. 12B shows the sealing member of FIG. 12A following retraction of the sealing member into the tubular body to which it is operatively coupled.
Figure 13:
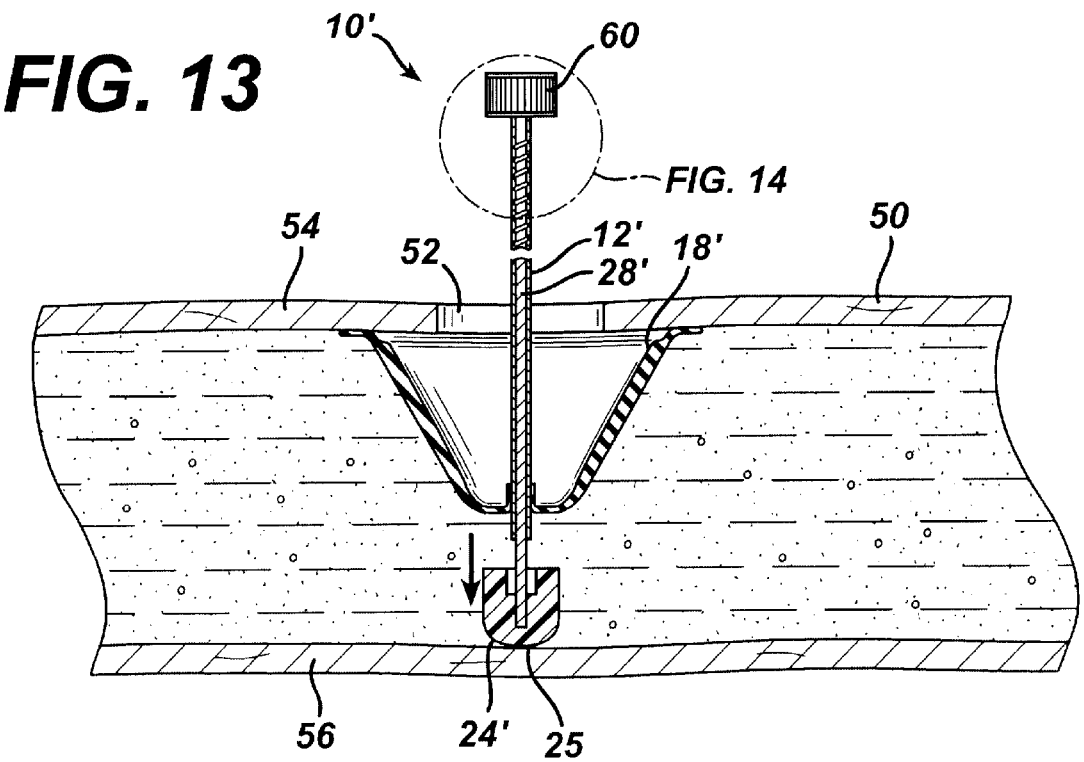
FIG. 13 is transverse cross-sectional view of an alternative embodiment of an intravascular hemostasis device constructed in accordance with the principles of the present invention.

FIGS. 12A–B illustrate an alternative embodiment of a sealing member 244. In particular, the sealing member 244 comprises three wire loops 250, 251, and 252, preferably made from Nitinol wire, which are shown extending out of a first elongated tubular member 240. The three (or more) loops 250, 251, and 252 are preferably spaced equidistant around the sealing member 244. As in the previous embodiment, the wire loops are preferably coated with a flexible, impermeable material such as polyurethane or silicone to make the sealing member 244 impermeable to the flow of blood. The wire loops are heat-treated into a preformed configuration as shown in FIG. 12A. Such a shape can be easily generated by shaping the shape-memory Nitinol wires into the desired configuration and heat-treating the wire in that configuration, e.g., heating the wire beyond a specific "memory temperature" to give the wire a memory capability for this shape. Contraction or expansion of the sealing member 244 is facilitated by using the shape-memory and flexibility of Nitinol to cause the sealing member 244 to collapse into its collapsed configuration upon retraction of the wires into the first elongated tubular member 240.

The wire loops 250, 251, and 252 are connected at their proximal ends to a second elongated tubular member 242 (e.g., a hypotube) which is axially movably disposed within the first elongated tubular member 240. Axial actuation of the second elongated tubular member 242 relative to the first elongated tubular member 240 can be accomplished in a number of ways. For example, the second elongated tubular member 242 can be threadably coupled to the first elongated tubular member 240 by a rotatable knob (not shown) at its proximal end such that rotational actuation of the second elongated tubular member 242 outside the vessel translates to axial movement of the sealing member 244 at the distal end portion of the device. Alternatively, a plunger-type mechanism, a spring-activated sliding-push button type mechanism (such as described above in connection with FIGS. 1–5), or a motor-driven linear actuator mechanism can be used to actuate the second elongated tubular member 242 to move axially relative to the first elongated tubular member 240. When the sealing member 244 is retracted into the first elongated tubular member 240 as shown in FIG. 12B, it assumes a narrow, collapsed configuration which is sized to allow the sealing member 244 to be inserted into and removed from the vessel through an opening therein. When the sealing member 244 is advanced beyond the distal end of the first elongated tubular member 240 (e.g., by axial movement of the second elongated tubular member 242), the sealing member assumes its preformed, heat treated expanded state in which the sealing member 244 is adapted to seal against the opening in the blood vessel as previously described and as shown in FIG. 12A.

According to further embodiments of the present inventioshown in FIGS. 13–17, the intravascular hemostasis device can be provided with various types of retention means to retain the sealing member in abutting engagement with the interior wall of the blood vessel thereby allowing substantially hands-free operation of the device. For example, as first illustrated in the embodiment of FIGS. 13 and 14 (wherein like numerals represent like elements to those described above), a retaining hub 24' similar to the support hub 24 of FIGS. 1–5 can be configured to move axially towards the interior wall of the blood vessel 56 opposite the wall 54 in which an opening 52 is created, until the support hub 24' abuts against and engages the wall. The retaining hub 24' preferably has a relatively smooth, blunt atraumatic distal tip engagement surface 25 as shown to prevent trauma or damage to the vessel wall 56 and to substantially minimize dislodgement of plaque or other atherosclerotic material from the vessel wall.

Figure 14:
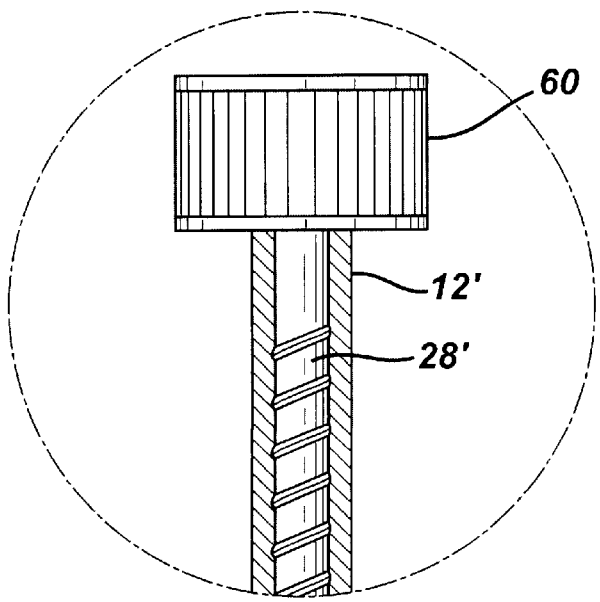
FIG. 14 is a detailed cross-sectional view of the proximal end portion of the intravascular hemostasis device of FIG. 13.

Fixation of the position of the retaining hub 24' once it contacts the interior vessel wall 56 opposite the inlet opening 52 can be accomplished in a number of ways. For example, as shown in FIG. 14, the second elongated tubular member 28' can be threadably coupled to the first elongated tubular member 12' and actuated by a rotatable knob 60 at the proximal end portion of the device 10' such that rotational actuation of the device 10' outside the vessel translates to gradual axial movement of the retaining hub 24' at the distal end portion of the device. Alternatively, a plunger-type mechanism, a spring-activated sliding-push button type mechanism (such as described above in connection with FIGS. 1–5), or a motor-driven linear actuator mechanism can be used to actuate the second elongated tubular member 28' to move axially relative to the first elongated tubular member 12' to accurately fixate the retaining hub 24' in abutting engagement with the interior wall of the blood vessel 56.

Figure 15:
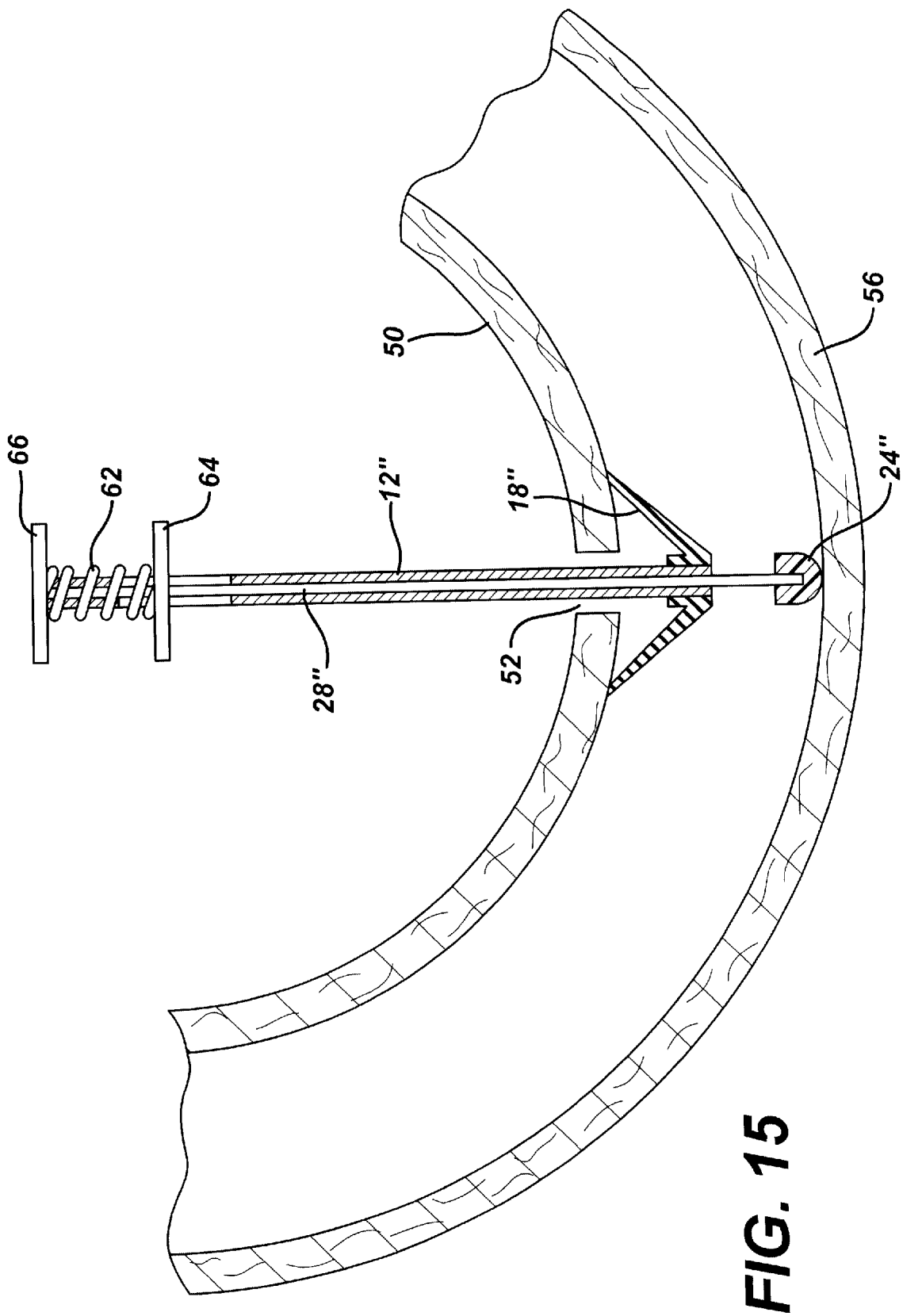
FIG. 15 is a transverse cross-sectional view of an alternative embodiment of an intravascular hemostasis device of the present invention in which the device is provided with a retention member which is adapted to retain the sealing member in abutting engagement with the interior wall of the vessel about the opening therein.

FIG. 15 illustrates an alternative embodiment of an intravascular hemostasis device which includes an alternative mechanism for retaining the retaining hub in abutting engagement with an interior wall of the vessel. In this particular embodiment, a retaining hub 24" is shown which has generally the same configuration as the retaining hub 24' described above with the exception that it is held in place in abutting engagement with the interior wall 56 of the vessel under the control of one or more springs. In particular, a spring 62 is located between an actuator body 64 (which is fixed to second elongated tubular member 28") and a handle 66 (which is configured to be grasped by the user during actuation of actuator body 64) and biases the actuator body 64 into an open configuration in which retaining hub 24" extends axially apart from the sealing member 18" and engages the interior wall 56 of the vessel as shown in FIG. 15. To retract the retaining hub 24" proximally towards the sealing member 18" (e.g., during insertion and removal of the device and/or to reposition the device within the vessel once it is inserted therein), the surgeon or surgeon's assistant, while grasping handle 66, can apply proximal finger pressure to the actuator body 64 to pull the actuator body towards the handle 66 and against the action of spring 62.

Figure 16:
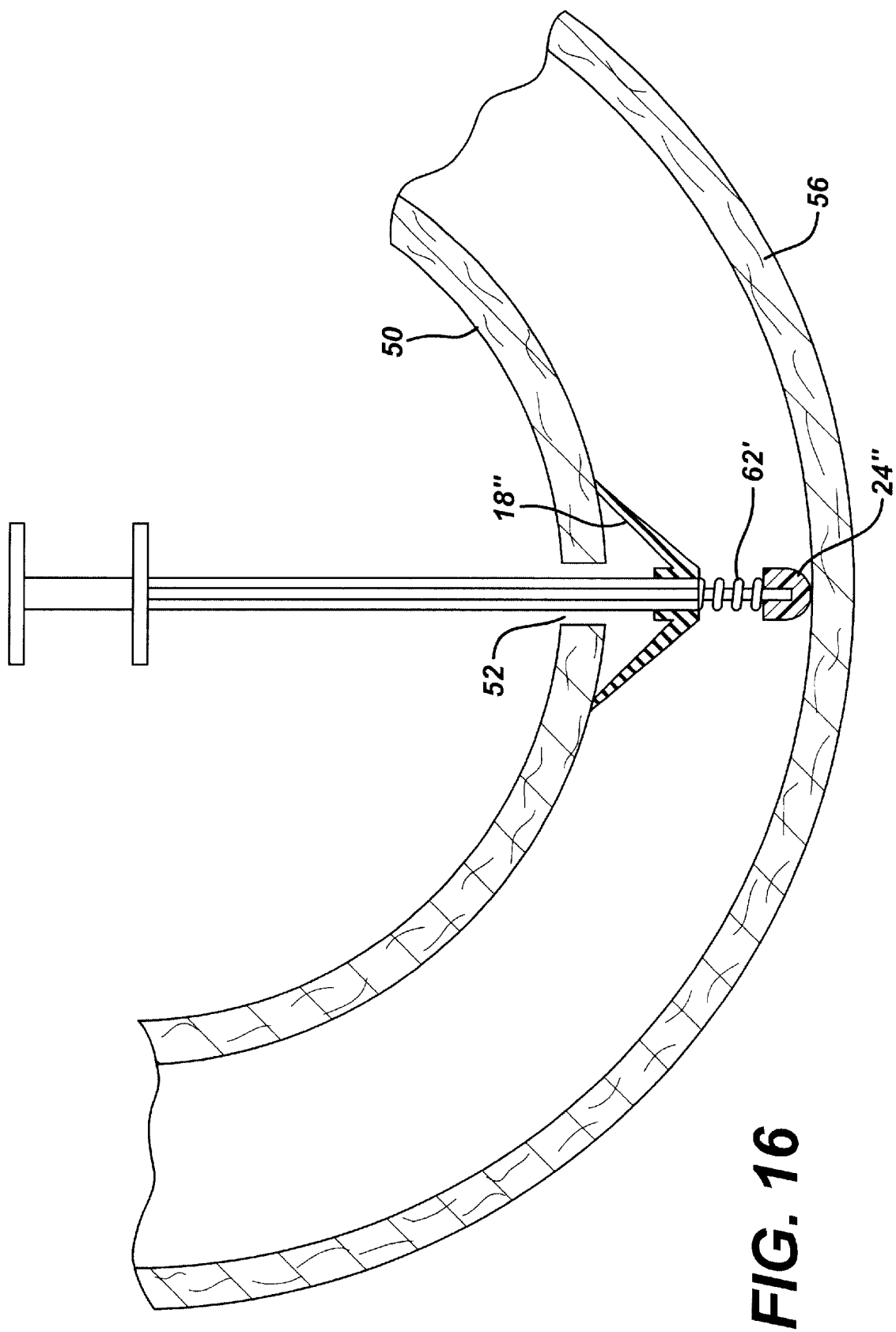
FIG. 16 is a transverse cross-sectional view of an alternative embodiment of an intravascular hemostasis device of the present invention in which the device is provided with a different configuration of the retention member of FIG. 15.

In an alternative embodiment, as shown in FIG. 16, a spring 62' can be positioned between the sealing member 18" and the retaining hub 24" and actuated in a similar manner as described above.

Figure 17:
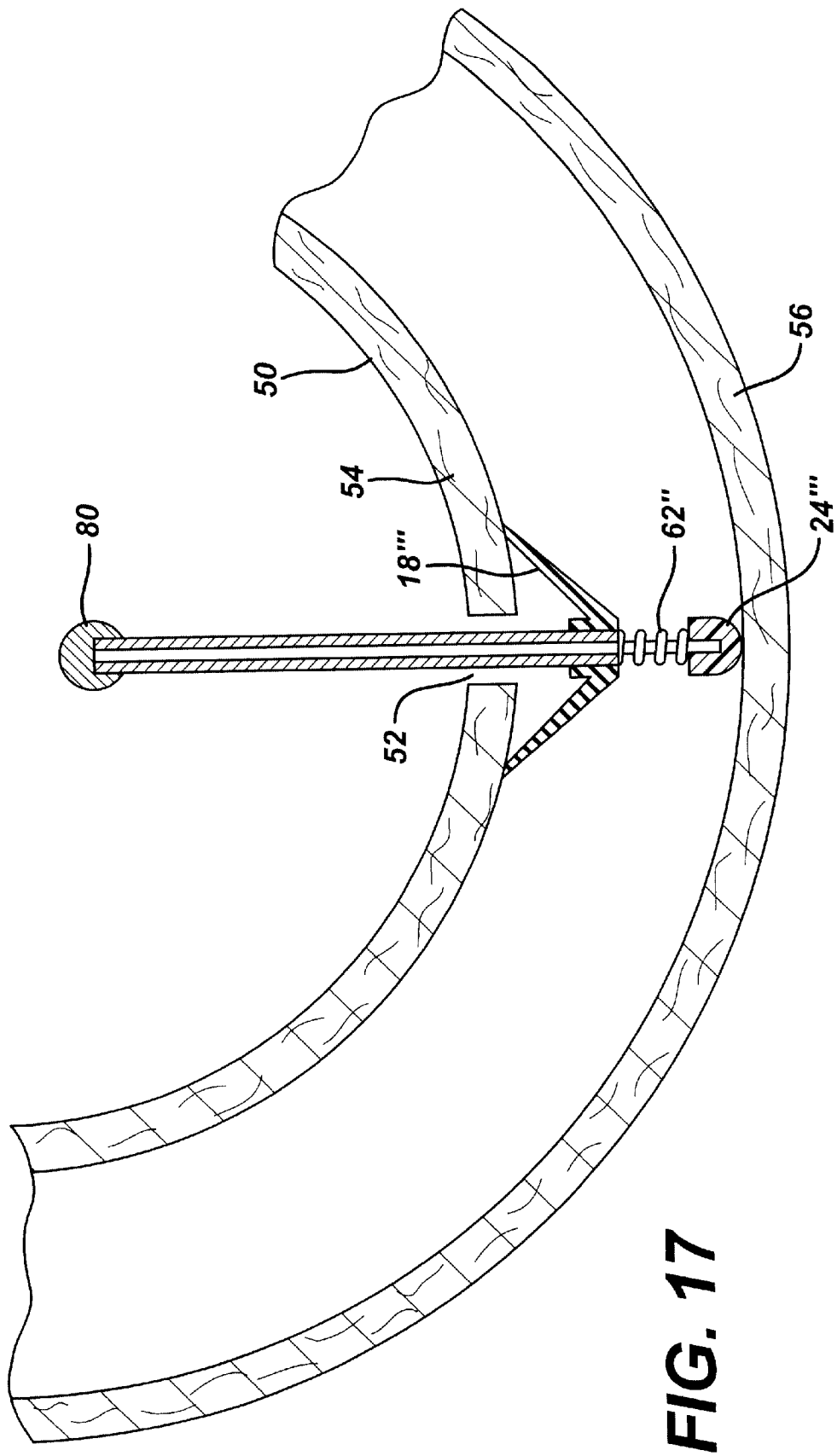
FIG. 17 is a transverse cross-sectional view of an alternative embodiment of an intravascular hemostasis device of the present invention in which the device is provided with a different configuration of the retention member of FIGS. 15 and 16.

Alternatively, as shown in FIG. 17, in a simplified configuration of the embodiment shown in FIGS. 15 and 16, the actuator can be removed and replaced by a simple grasping hub 80. Similar to the previous embodiment, a spring 62" is inserted between the retaining hub 24'" and the sealing member 18'". The spring 62" serves to bias the sealing member 18'" and the retaining hub 24'" into relative abutting engagement with the internal walls of the vessel in the expanded configuration of the sealing member within the vessel. The sealing member 18'" can be removed from the vessel in a similar fashion to previous embodiments (e.g., by inversion of the sealing member and subsequent radial compression of the sealing member as it is removed through the opening in the vessel wall).

Optionally, the various devices described above in connection with FIGS. 13–17 could be provided with some type of feedback mechanism to indicate to the user of the device when the retaining hub engages with the vessel wall. This could be accomplished in a number of ways. For example, the distal tip of the retaining hub could be provided with a pressure sensor to sense contact with the vessel wall, or the second elongated tubular member to which the retaining hub is coupled could be provided with a torque or strain sensor or similar device coupled to the tubular member which is capable of detecting torque to a high sensitivity applied to a rotary shaft. Examples of such torque sensors are fully described, for example, in U.S. Pat. No. 5,831,180 to Tanaka et al., the entire contents of which are incorporated by reference herein. The retaining hub may also be provided with a suction port (not shown in the drawings) through the retaining hub which fluidly communicates with the interior of the second elongated tubular member. A suction force may be applied through the second elongated tubular member and through the retaining hub and suction port to help retain and fixate the retaining hub in abutting engagement with the internal wall 56 of the vessel.

Figure 18:
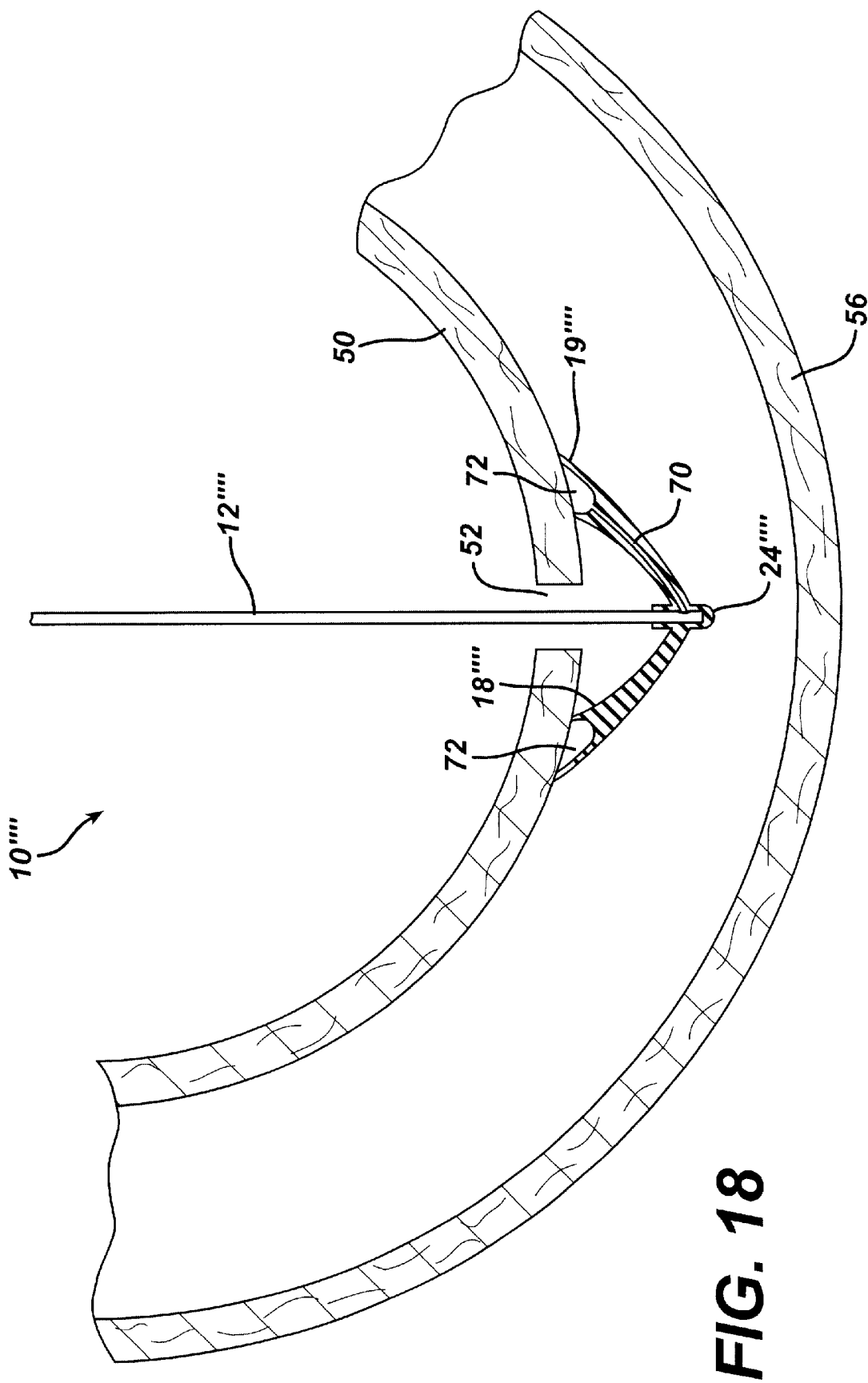
FIG. 18 is a transverse cross-sectional view of an alternative embodiment of an intravascular hemostasis device of the present invention in which the device is provided with a suction capability which is configured to retain the sealing member in abutting engagemen with the interior wall of the vessel about the opening therein.

In another alternative embodiment of the invention shown in FIG. 18, the sealing member of the intravascular hemostasis device can be provided with its own suction capability to allow the sealing member to be retained in sealing engagement with the interior wall of the vessel proximate the opening therein. The retaining hub in this embodiment could be used as a support hub to provide support to the sealing member in its expanded configuration similar to the support hub 24 of FIG. 1, or the support hub could be removed. The intravascular hemostasis device 10"" (which is similar in most respects to the device 10 of FIGS. 1–5) includes a flexible sealing member 18"" which has a suction channel 70 formed therein which fluidly communicates with an annular channel or port 72 formed into the circumferential rim portion 19"" of the sealing member 18"". Suction channel 70 also fluidly communicates with the interior of elongated tubular member 12"". A suction force can be transmitted down the elongated tubular member 12"" from an external vacuum source (not shown) in a conventional manner when the sealing member 18"" contacts the interior wall of the vessel around the opening, to retain the sealing member 18"" in abutting, sealing engagement with the interior wall. An example of a suitable vacuum control assembly which can be mounted to the handle of the device 10"" for creating a suction force within the sealing member can be found in co-pending patent application Ser. No. 09/124,534 entitled "Surgical Cutting Instrument and Method of Use," filed on Jul. 29, 1998 and invented by Michael Hogendijk, the entire contents of which are incorporated by reference herein (See, for example, FIGS. 1 and 2A therein (vacuum control assembly 50)). Such a configuration allows for hands-free operation of the device while the sealing member 18"" is in its expanded, sealing configuration. To remove the sealing member 18"" from the vessel, the suction force can be removed and the sealing member removed from the vessel in a similar fashion as described previously in connection with FIGS. 1–5. The proximal portion of the device, including the handle and actuator for support hub 24"" (if used), may be constructed in accordance with the embodiment of FIGS. 1–5 and are not shown for clarity and convenience.

In each of the previous described embodiments, the sealing member is configured to be inserted and removed from the vessel through the actual anastomosis site (e.g., through the opening in the aorta where the free graft vessel is attached). However, it is also within the scope of the present invention for the sealing member to be configured to be inserted and removed through a separate opening other than the opening where the anastomosis is to be made. The advantage of this particular embodiment is that the device remains out of the operative field in which the surgeon works to provide the surgeon with an unobstructed surgical field in which to operate.

Figure 19:
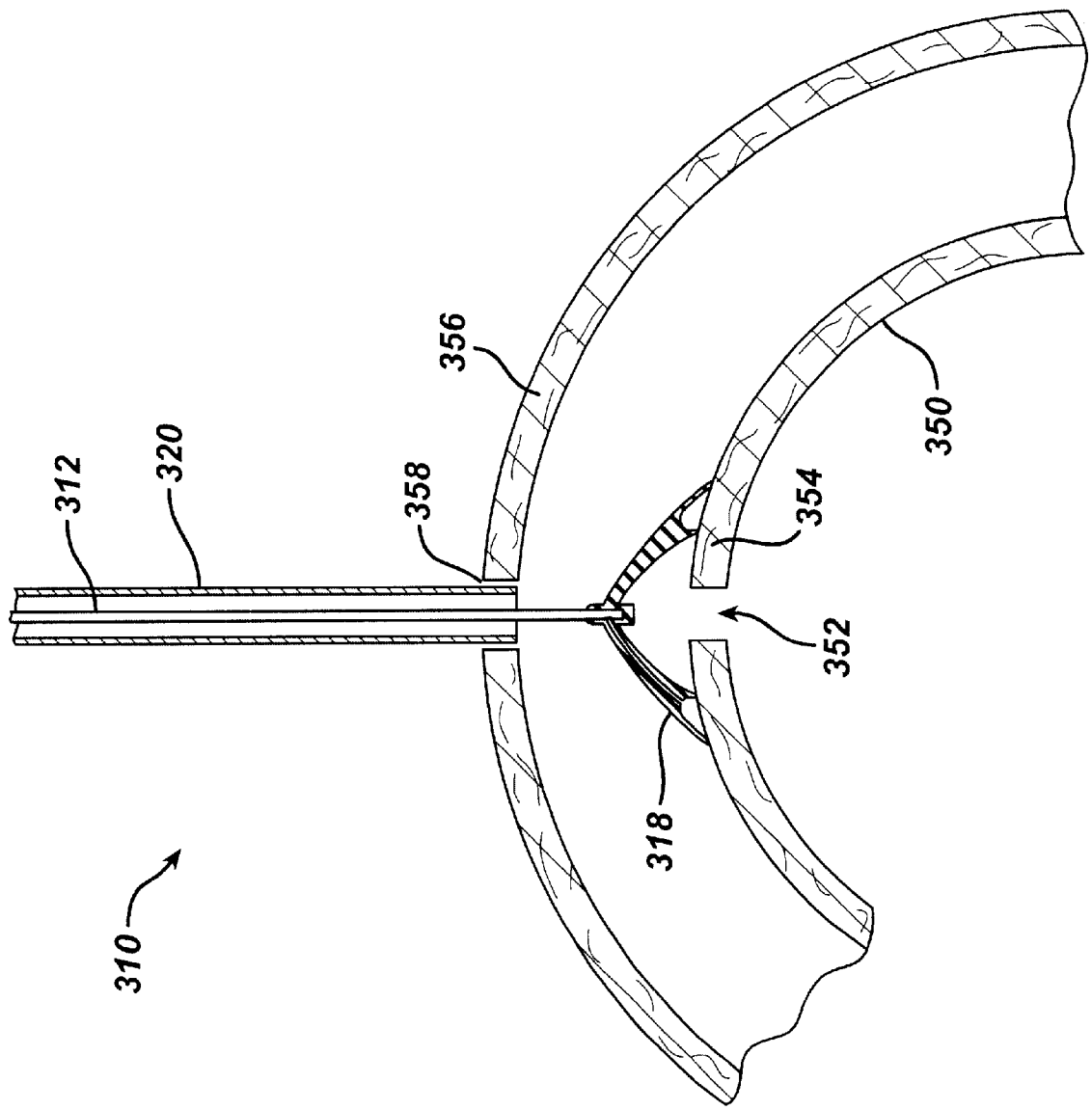
FIG. 19 is a transverse cross-sectional view of an alternative embodiment of an intravascular hemostasis device of the present invention which is configured to be inserted into an opening which is separate from the opening where the anastomosis graft is to be made.

For example, in the embodiment of FIG. 19, the device 310 includes a sealing member 318 which is configured to be inserted into a vessel 350-through an opening 358 in the vessel wall 356 which is located opposite to the opening 352 where the anastomosis graft is to be made. Therefore, the sealing member seals the anastomosis opening while not obstructing in any substantial way the surgeon's access to the operative site. The sealing member 318 is similar in configuration to the sealing member 18 of the embodiment of FIGS. 1–5 with the primary difference being that the sealing member has a natural pre-formed expanded state which is substantially a mirror image of the pre-formed expanded state of the sealing member 18, i.e., the sealing member 318 is inverted with respect to sealing member 18 in its natural, pre-formed expanded state. The sealing member 318 can be inserted into the vessel with the use of a separate introducer 320. A handle (and an optional actuator to actuate a retaining hub located adjacent the sealing member) is attached to the proximal end of the elongated tubular body 312. The handle (and optional actuator) can be the same as described above and are not illustrated. The sealing member 318 can also include a suction capability as described above in connection with FIG. 18 and as shown in FIG. 19.

To operate the device 310 of FIG. 19, an opening 358 is first made in the vessel wall 356, such as the aorta, opposite to the location of where a proximal anastomosis incision is to be made. The sealing member 318 is inserted into the vessel while encapsulated within introducer 320. Once the sealing member 318 and distal end portion of the introducer 320 are inserted within the vessel, the introducer is retracted back over the sealing member (or the sealing member is moved axially relative to the introducer by applying forward pressure to elongated tubular body 312 while holding introducer 320 stationary) until the sealing member 318 extends a short distance beyond the distal end of the introducer. One or more purse string sutures can be passed through the vessel wall 356 about introducer 320 to help secure the introducer in place and to prevent blood loss through opening 358. In this configuration, an opening 352 is then made in vessel wall 354 where an anastomosis graft is to be made. The sealing member 318 can then be moved into sealing engagement with the internal wall of the vessel about the opening 352 by moving the elongated tubular member 312 axially relative to introducer 320 until the sealing member engages the wall about the opening 352. If necessary, a suction force can be applied to the sealing member 318 to retain the sealing member in abutting engagement with the interior wall of the vessel. The anastomosis procedure can be accomplished with the sealing member in place adjacent the opening in the vessel. To withdraw the sealing member 318 from the vessel, the elongated tubular member 312 can be moved proximally (e.g., away from the vessel) while holding the introducer 320 stationary to withdraw the sealing member back into the introducer. The introducer 320 and the sealing member 318 can then be removed from the vessel after the anastomosis procedure is completed.

All references cited herein are expressly incorporated by reference.

The above is a detailed description of one or more particular embodiments of the invention. It is recognized and understood that departures from the disclosed embodiments may be made within the scope of the invention and that obvious modifications will occur to a person of ordinary skill in the art. The full scope of the invention is set out in the claims that follow and their equivalents. Accordingly, the claims and specification should not be construed to unduly narrow the full scope of protection to which the invention is entitled.

What is claimed is:

1. An intravascular hemostasis device comprising:
   at least a first elongated tubular member having a proximal end portion and a distal end portion; and
   a flexible, deformable sealing member coupled to the distal end portion of the elongated tubular member which has at least a first preformed expanded state, said sealing member adapted to at least partially radially compressible to at least a first compressed state for insertion of the sealing member into an opening in a wall of a blood vessel by the wall surrounding the opening, said sealing member being radially self-expandable from said first compressed state to said first expanded state after the sealing member is inserted into the opening in the vessel in which the sealing member is adapted to seal against the inner wall of the blood vessel around the opening.

2. The intravascular hemostasis device of claim 1 wherein said sealing member is made from a biocompatible material.

3. The intravascular hemostasis device of claim 2 wherein said biocompatible material comprises a plastic material.

4. The intravascular hemostasis device of claim 3 wherein said plastic material comprises silicone.

5. The intravascular hemostasis device of claim 1 wherein said sealing member has a pre-formed cup shaped configuration in said first expanded state in which said sealing member has a circumferential rim portion which is adapted to form a seal against the inner wall of the blood vessel around the opening.

6. The intravascular hemo stasis device of claim 5 wherein said circumferential rim portion has a diameter which is at least two times a diameter of the opening in the wall of the blood vessel.

7. The intravascular hemostasis device of claim 5 wherein said circumferential rim portion has a diameter of between about 4 and 20 mm.

8. The intravascular hemostasis device of claim 1 further comprising a support member operatively coupled to or immediately adjacent to said sealing member.

9. The intravascular hemostasis device of claim 8 wherein said support member comprises a support hub located adjacent to said sealing member.

10. The intravascular hemostasis device of claim 1 further comprising means for retaining the sealing member in abutting engagement with an interior wall of the blood vessel.

11. The intravascular hemostasis device of claim 1 further comprising means for retaining the sealing member adjacent to the internal wall of the vessel around the opening.

12. The intravascular hemostasis device of claim 11 wherein said retaining means comprises at least one suction port through the sealing member, connectable with a vacuum source.

13. The intravascular hemostasis device of claim 12 wherein said suction port communicates with an annular channel formed in a circumferential rim portion of the sealing member.

14. An intravascular hemostasis device, comprising:
at least a first elongated tubular member having a proximal end portion and a distal end portion;
a flexible, deformable sealing member coupled to the distal end portion of the elongated tubular member which has at least a first pre-formed expanded state, said sealing member being at least partially radially compressible to at least a first compressed state for insertion of the sealing member into an opening in a wall of a blood vessel, said sealing member being radially self-expandable from said first compressed state to said first expanded state after the sealing member is inserted into the opening in the vessel in which the sealing member is adapted to seal against an inner wall of the blood vessel around the opening;
said sealing member has a pre-formed cup shaped configuration in said first expanded state in which said sealing member has a circumferential rim portion which is adapted to form a seal against the inner wall of the blood vessel around the opening; and
wherein said circumferential rim portion has a material thickness which is less than a thickness of a remaining portion of the sealing member.

15. An intravascular hemostasis device, comprising:
at least a first elongated tubular member having a proximal end portion and a distal end portion;
a flexible, deformable sealing member coupled to the distal end portion of the elongated tubular member which has at least a first pre-formed expanded state, said sealing member being at least partially radially compressible to at least a first compressed state for insertion of the sealing member into an opening in a wall of a blood vessel, said sealing member being radially self-expandable from said first compressed state to said first expanded state after the sealing member is inserted into the opening in the vessel in which the sealing member is adapted to seal against an inner wall of the blood vessel around the opening; and
wherein said sealing member is moveable to an inverted configuration to facilitate its removal from the blood vessel in which said sealing member has a second expanded state which is a mirror image of said first expanded state when a sufficient force is applied to said sealing member.

16. The intravascular hemostasis device of claim 15 wherein said first and second expanded states correspond to respective natural positions of the sealing member.

17. The intravascular hemostasis device of claim 15 wherein an inner wall of said vessel exerts said force to the sealing member to invert said sealing member from said first expanded state to said second expanded state upon movement of said at least first elongated tubular member proximally relative to said vessel.

18. The intravascular hemostasis device of claim 17 wherein said sealing member is at least partially radially compressible from said second expanded state to a second compressed state to facilitate removal of the sealing member from the blood vessel through said opening in the blood vessel.

19. An intravascular hemostasis device, comprising:
at least a first elongated tubular member having a proximal end portion and a distal end portion;
a flexible, deformable sealing member coupled to the distal end portion of the elongated tubular member which has at least a first pre-formed expanded state, said sealing member being at least partially radially compressible to at least a first compressed state for insertion of the sealing member into an opening in a wall of a blood vessel, said sealing member being radially self-expandable from said first compressed state to said first expanded state after the sealing member is inserted into the opening in the vessel in which the sealing member is adapted to seal against an inner wall of the blood vessel around the opening;
a support member operatively coupled to or immediately adjacent to said sealing member, said support member comprises a plurality of wires movably embedded within said sealing member.

20. The intravascular hemostasis device of claim 19 wherein said plurality of wires are circumferentially spaced about said sealing member.

21. The intravascular hemostasis device of claim 20 wherein said plurality of wires are equally spaced circumferentially around the sealing member.

22. The intravascular hemostasis device of claim 20 further comprising an actuator operatively coupled to the proximal end portion of said elongated tubular member, said actuator being coupled to said plurality of wires and being operable to withdraw said plurality of wires from said sealing member to facilitate removal of the sealing member from the blood vessel through the opening in the wall of the blood vessel.

23. An intravascular hemostasis device, comprising:
at least a first elongated tubular member having a proximal end portion and a distal end portion;
a flexible, deformable sealing member coupled to the distal end portion of the elongated tubular member which has at least a first pre-formed expanded state, said sealing member being at least partially radially compressible to at least a first compressed state for insertion of the sealing member into an opening in a wall of a blood vessel, said sealing member being radially self-expandable from said first compressed state to said first expanded state after the sealing member is inserted into the opening in the vessel in which the sealing member is adapted to seal against an inner wall of the blood vessel around the opening;
a support member operatively coupled to or immediately adjacent to said sealing member; said support member comprises a support hub located adjacent to said sealing member; and
a second elongated tubular member slidably coupled to said first elongated tubular member, said support hub being coupled to a distal end portion of said second elongated tubular member.

24. The intravascular hemostasis device of claim 23 further comprising an actuator operatively coupled to said second elongated tubular member.

25. The intravascular hemostasis device of claim 24 wherein said support hub is moveable axially relative to said sealing member upon actuation of said actuator which facilitates removal of said sealing member from the blood vessel through the opening in the wall of the blood vessel.

26. The intravascular hemostasis device of claim 25 further comprising a spring which is adapted to bias said actuator into a closed, retracted configuration in which the support hub engages the sealing member.

27. An intravascular hemostasis device, comprising:
- at least a first elongated tubular member having a proximal end portion and a distal end portion;
- a flexible, deformable sealing member coupled to the distal end portion of the elongated tubular member which has at least a first pre-formed expanded state, said sealing member being at least partially radially compressible to at least a first compressed state for insertion of the sealing member into an opening in a wall of a blood vessel, said sealing member being radially self-expandable from said first compressed state to said first expanded state after the sealing member is inserted into the opening in the vessel in which the sealing member is adapted to seal against an inner wall of the blood vessel around the opening;
- means for retaining the sealing member in abutting engagement with an interior wall of the blood vessel; and
- a second elongated tubular member slidably coupled to said first elongated tubular member, wherein said retaining means comprises a distal tip portion coupled to said second elongated tubular member, said distal tip portion being configured to abut against an interior wall of the blood vessel opposite the wall having the opening therein when said second elongated tubular member is moved axially relative to said first elongated tubular member.

28. The intravascular hemostasis device of claim 27 further comprising at least one spring which is adapted to bias said distal tip portion into engagement with the interior wall of the vessel opposite the wall with the opening therein.

29. The intravascular hemostasis device of claim 28 wherein said spring is located between said sealing member and said distal tip portion.

30. An intravascular hemostasis device comprising:
- a first elongated tubular member;
- a second elongated tubular member rotatably coupled to said first elongated tubular member;
- a flexible sealing member coupled to distal end portions of said first and second elongated tubular members, said sealing member being moveable between a narrow, collapsed configuration in which said sealing member is adapted to be inserted into and removed from a blood vessel through an opening in a wall of the blood vessel, and an expanded configuration in which the sealing member is adapted to form a seal against an inner wall of the blood vessel around the opening; and
- wherein said sealing member is selectively adjustable between said narrow, collapsed configuration and said expanded configuration upon relative rotational movement of said first and second elongated tubular members from outside the blood vessel.

31. An intravascular hemostasis device comprising:
- a first elongated tubular member;
- a second elongated tubular member rotatably coupled to said first elongated tubular member;
- a flexible sealing member coupled to distal end portions of said first and second elongated tubular members, said sealing member being moveable between a narrow, collapsed configuration in which said sealing member is adapted to be inserted into and removed from a blood vessel through an opening in a wall of the blood vessel, and an expanded configuration in which the sealing member is adapted to form a seal against an inner wall of the blood vessel around the opening;
- wherein said sealing member is selectively adjustable between said narrow, collapsed configuration and said expanded configuration upon relative axial movement of said first and second elongated tubular members from outside the blood vessel; and
- wherein said sealing member comprises a wire or ribbon which is spiraled about the distal end portions of said first and second elongated tubular members.

32. The device of claim 31 wherein said wire or ribbon is at least partially coated with a polyurethane material.

33. The device of claim 31 wherein said wire or ribbon is made from Nitinol.

34. The device of claim 31 further comprising an actuator coupled to a proximal end portion of said second elongated tubular member which is operable to rotate said second elongated tubular member relative to said first elongated tubular member to selectively move said wire or ribbon between said narrow, collapsed configuration and said expanded configuration.

35. An intravascular hemostasis device comprising:
- a first elongated tubular member;
- a second elongated tubular member movably coupled to said first elongated tubular member;
- a flexible sealing member coupled to a distal end portion of said second elongated tubular member, said sealing member being moveable between a narrow, collapsed configuration in which said sealing member is adapted to be inserted into and removed from a blood vessel through an opening in a wall of the blood vessel, and an expanded configuration in which the sealing member is adapted to form a seal against an inner wall of the blood vessel around the opening;
- wherein said sealing member is selectively adjustable between said narrow, collapsed configuration and said expanded configuration upon relative axial movement of said first and second elongated tubular members from outside the blood vessel; and
- wherein said sealing member comprises a plurality of wire loops that are coated with a polyurethane material.

36. The intravascular hemostasis device of claim 35 wherein said plurality of wire loops are pre-formed into a natural expanded configuration.

37. The intravascular hemostasis device of claim 36 wherein said wire loops are made from a Nitinol material.

38. The intravascular hemo stasis device of claim 36 wherein said sealing member comprises at least three wire loops which are circumferentially spaced equidistant about the sealing member.

39. An intravascular hemostasis device comprising:
- a first elongated tubular member having a proximal end portion and a distal end portion;
- a sealing member coupled to the distal end portion, the sealing member having at least a first preformed expanded state, the sealing member being at least partially radially compressible to at least a first compressed state for insertion of the sealing member into an opening in a wall of a blood vessel, the sealing member being radially self-expandable from the first compressed state to the first expanded state after the sealing member is inserted into the opening in the vessel, the sealing member being adapted to seal against the inner wall of the blood vessel around the opening; and
- a support member constructed to engage the sealing member to facilitate in maintaining the sealing member in the first expanded state.

40. The intravascular hemostasis device of claim 39, being operatively coupled to the sealing member.

41. The intravascular hemostasis device of claim 40, wherein the support member comprises a plurality of wires disposed within the sealing member.

42. The intravascular hemostasis device of claim 41, wherein the plurality of wires are circumferentially spaced within the sealing member.

43. The intravascular hemostasis device of claim 41, comprising an actuator operatively coupled to the proximal eyed portion of the first elongated tubular member, the actuator being coupled to the plurality of wires and being operable to withdraw the plurality of wires from the sealing member.

44. The intravascular hemostasis device of claim 39, wherein the support member is positioned adjacent the sealing member.

45. The intravascular hemostasis device of claim 44, wherein the support member comprises a support hub located distal to the sealing member.

46. The intravascular hemostasis device of claim 45, comprising a second elongated tubular member slidably coupled to the first elongated tubular member, the support hub being coupled to a distal end portion of the second elongated tubular member.

47. The intravascular hemostasis device of claim 46, comprising an actuator operatively coupled to the second elongated tubular member.

48. The intravascular hemostasis device of claim 47, wherein the support hub is moveable axially relative to the sealing member upon actuation of the actuator.

49. The intravascular hemostasis device of claim 48, wherein the support hub is moveable distally relative to the sealing member upon actuation of the actuator.

50. The intravascular hemostasis device of claim 46, comprising a spring which is adapted to bias the actuator to a configuration in which the support hub engages the sealing member.

51. An intravascular hemostasis device comprising:

an elongated tubular member having a proximal end portion and a distal end portion;

a flexible, deformable sealing member coupled to the distal end portion of the elongated tubular member, the sealing member having at least an expanded state, the sealing member being at least partially radially compressible to at least a compressed state for insertion of the sealing member into an opening in a wall of a blood vessel, the sealing member being radially self-expandable from the compressed state to the expanded state after the sealing member is inserted into the opening in the vessel, the sealing member being adapted to seal against the inner wall of the blood vessel around the opening; and means for retaining the sealing member adjacent to the internal wall of the vessel around the opening.

52. The intravascular hemostasis device of claim 51, wherein the retaining means comprises a suction source and a suction channel connectable to the suction source.

53. The intravascular hemostasis device of claim 51, wherein the sealing member has at least one suction opening that is in fluid communication with the suction channel.

54. The intravascular hemostasis device of claim 51, wherein the elongated tubular member is hollow and the retaining means comprises a suction source and a suction channel, the hollow tubular member being connected at a distal end to the suction channel and being connectable at a proximal end to the suction source.

55. The intravascular hemostasis device of claim 54, wherein the sealing member has a circumferential rim portion, and the suction channel comprises an annular channel formed in the circumferential rim portion.

* * * * *